US008779202B2

(12) United States Patent
Elmendorf et al.

(10) Patent No.: US 8,779,202 B2
(45) Date of Patent: Jul. 15, 2014

(54) COMPOSITIONS AND METHODS FOR THE TREATMENT OF GIARDIASIS

(75) Inventors: Heidi G. Elmendorf, Rockville, MD (US); Colleen D. Walls, Chevy Chase, MD (US); Christian Wolf, Arlington, VA (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 13/513,768

(22) PCT Filed: Dec. 2, 2010

(86) PCT No.: PCT/US2010/058757

§ 371 (c)(1),
(2), (4) Date: Jun. 4, 2012

(87) PCT Pub. No.: WO2011/068987

PCT Pub. Date: Jun. 9, 2011

(65) Prior Publication Data

US 2012/0283267 A1 Nov. 8, 2012

Related U.S. Application Data

(60) Provisional application No. 61/266,660, filed on Dec. 4, 2009.

(51) Int. Cl.
*C07C 211/00* (2006.01)

(52) U.S. Cl.
USPC .......... 564/305

(58) Field of Classification Search
None
See application file for complete search history.

(56) References Cited

U.S. PATENT DOCUMENTS 4,523,958 A 6/1985 Fechner et al.

FOREIGN PATENT DOCUMENTS

WO 03/031507 4/2003

OTHER PUBLICATIONS

Searcey et al., "A mild procedure for the production of secondary amines from oximes and benzisoxazoles," Tetrahedron Letters, 44: 6745-6747 (2003).
Smith, P.D., C.O. Elson, D.B. Keister, and T.E. Nash, "Human host response to *Giardia lamblia*. I. Spontaneous killing by mononuclear leukocytes in vitro." J Immunol, 1982. 128(3): p. 1372-6.
Sousa, M.C., C.A. Goncalves, V.A. Bairos, and J. Poiares-Da-Silva, "Adherence of *Giardia lamblia* trophozoites to Int-407 human intestinal cells." Clin Diagn Lab Immunol, 2001. 8(2): p. 258-65.
Tikhonova, I.G., C.S. Sum, S. Neumann, S. Engel, B.M. Raaka, S. Costanzi, and M.C. Gershengorn, "Discovery of novel agonists and antagonists of the free fatty acid receptor 1 (FFAR1) using virtual screening." J Med Chem, 2008. 51(3): p. 625-33.
Tochtrop, G.P. and R.W. King, "Target identification strategies in chemical genetics." Comb Chem High Throughput Screen, 2004. 7(7): p. 677-88.
Upcroft, J.A., L.A. Dunn, J.M. Wright, K. Benakli, P. Upcroft, and P. Vanelle, "5-Nitroimidazole drugs effective against metronidazole-resistant *Trichomonas vaginalis* and *Giardia duodenalis*." Antimicrob Agents Chemother, 2006. 50(1): p. 344-7.
Upcroft, P. and J.A. Upcroft, "Drug targets and mechanisms of resistance in the anaerobic protozoa." Clin Microbiol Rev, 2001. 14(1): p. 150-64.
Vale, R.D., "The molecular motor toolbox for intracellular transport." Cell, 2003. 112(4): p. 467-80.
Vogt, A. and J.S. Lazo, "Chemical complementation: a definitive phenotypic strategy for identifying small molecule inhibitors of elusive cellular targets." Pharmacol Ther, 2005. 107(2): p. 212-21.
WHO/UNICEF, "Global Water Supply and Sanitation Assessment 2000 Report," in WHO/UNICEF Joint Monitoring Programme for Water Supply and Sanitation. 2000.
Woodgate et al., "Synthesis of dioxazaborocines from N-substituted-bis(2-hydroxyaryl)aminomethylamines," Journal of Organometallic Chemistry, 592(2):180-193 (1999).
Wright, J.M., L.A. Dunn, P. Upcroft, and J.A. Upcroft, "Efficacy of antigiardial drugs." Expert Opin Drug Saf, 2003. 2(6): p. 529-41.
Yarrow, J.C., Y. Feng, Z.E. Perlman, T. Kirchhausen, and T.J. Mitchison, "Phenotypic screening of small molecule libraries by high throughput cell imaging." Comb Chem High Throughput Screen, 2003. 6(4): p. 279-86.
Yoder, J.S. and M.J. Beach, "Giardiasis surveillance—United States, 2003-2005." MMWR Surveill Summ, 2007. 56(7): p. 11-8.
Zaat JO, M.T., Assendelft WJ, "A systematic review on the treatment of Giardiasis." Trop Med Int Health, 1997. 2: p. 63-82.
Zaat JOM, Mank ThG, Assendelft WJJ, "Drugs for treating Giardiasis." Cochrane Database of Systematic Reviews 1998, Issue 3. Art No. CD000217.
Adam, R.D., Biology of *Giardia lamblia*. Clin Microbiol Rev, 2001. 14(3): p. 447-75.
Bonilla-Santiago, R., Z. Wu, L. Zhang, and G. Widmer, Identification of growth inhibiting compounds in a *Giardia lamblia* high-throughput screen. Mol Biochem Parasitol, 2008. 162(2): p. 149-54.
Brandonisio, O., "Waterborne transmission of *Giardia* and *Cryptosporidium*." Parassitologia, 2006. 48(1-2): p. 91-4.
Burdine, L. and T. Kodadek, "Target identification in chemical genetics: the (often) missing link." Chem Biol, 2004. 11 (5): p. 593-7.
Buret, A., N. denHollander, P.M. Wallis, D. Befus, and M.E. Olson, "Zoonotic potential of giardiasis in domestic ruminants." J Infect Dis, 1990. 162(1): p. 231-7.
Buret, A.G., K. Mitchell, D.G. Muench, and K.G. Scott, "*Giardia lamblia* disrupts tight junctional ZO-1 and increases permeability in non-transformed human small intestinal epithelial monolayers: effects of epidermal growth factor." Parasitology, 2002. 125(Pt 1): p. 11-9.

(Continued)

*Primary Examiner* — Clinton Brooks
(74) *Attorney, Agent, or Firm* — Kilpatrick, Townsend & Stockton LLP

(57) ABSTRACT

Methods of treating exposure to *Giardia lamblia* and/or giardiasis and methods of antagonizing *Giardia lamblia* attachment to the intestinal wall of a subject are described herein.

3 Claims, 1 Drawing Sheet

(56) References Cited

OTHER PUBLICATIONS

Burke et al, "Synthesis and Study of Mannich Bases from 2-Naphthol and Primary Amines," Journal of Organic Chemistry, 29(2): 407-410 (1964).
Correa, G. and M. Benchimol, *Giardia lamblia* behavior under cytochalasins treatment. Parasitol Res, 2006. 98(3): p. 250-6.
Crossley, R. and D.V. Holberton, "Characterization of proteins from the cytoskeleton of *Giardia lamblia*." J Cell Sci, 1983. 59: p. 81-103.
Drouin, G., "Nonrandom CpG mutations affect the synonymous codon usage of moderately GC-rich single copy actin genes." J Mol Evol, 1991. 33(3): p. 237-40.
Drouin, G., M. Moniz de Sa, and M. Zuker, "The *Giardia lamblia* actin gene and the phylogeny of eukaryotes." J Mol Evol, 1995. 41(6): p. 841-9.
Elmendorf, H.G., S.C. Dawson, and J.M. McCaffery, "The cytoskeleton of *Giardia lamblia*." Int J Parasitol, 2003. 33(1): p. 3-28.
Engel, S., A.P. Skoumbourdis, J. Childress, S. Neumann, J.R. Deschamps, C.J. Thomas, A.O. Colson, S. Costanzi, and M.C. Gershengorn, "A virtual screen for diverse ligands: discovery of selective G protein-coupled receptor antagonists." J Am Chem Soc, 2008. 130(15): p. 5115-23.
Faubert, G.M., P. Lee, and A. Abdul-Wahid, "*Giardia duodenalis*," in Infections of the gastrointestinal tract, P.D.S. M. J. Blaser, J. I. Ravdin, H. B. Greenberg, and R. L. Guerrant Editor. 2002, LWW Publishing Co: New York. p. 978-1006.
Fenteany, G. and S. Zhu, "Small-molecule inhibitors of actin dynamics and cell motility." Curr Top Med Chem, 2003. 3 (6): p. 593-616.
Fiser, A. and A. Sali, "Modeller: generation and refinement of homology-based protein structure models." Methods Enzymol, 2003. 374: p. 461-91.
Furness, B.W., M.J. Beach, and J.M. Roberts, "Giardiasis surveillance—United States, 1992-1997." MMWR CDC Surveill Summ, 2000. 49(7): p. 1-13.
Gadelha, A.P., R. Travassos, and L.H. Monteiro-Leal, "The evaluation of a semiautomated computer method to determine the effects of DMSO on *Giardia lamblia*-intestinal cell interaction." Parasitol Res, 2007. 101(5): p. 1401-6.
Gardner, T.B. and D.R. Hill, "Treatment of giardiasis." Clin Microbiol Rev, 2001. 14(1): p. 114-28.
Giganti, A. and E. Friederich, "The actin cytoskeleton as a therapeutic target: state of the art and future directions." Prog Cell Cycle Res, 2003. 5: p. 511-25.
Groves, J.T., R. Parthasarathy, and M.B. Forstner, "Fluorescence imaging of membrane dynamics." Annu Rev Biomed Eng, 2008. 10: p. 311-38.
Hansen, W.R., O. Tulyathan, S.C. Dawson, W.Z. Cande, and D.A. Fletcher, "*Giardia lamblia* attachment force is insensitive to surface treatments." Eukaryot Cell, 2006. 5(4): p. 781-3.
Holberton, D.V., "Arrangement of subunits in microribbons from *Giardia*." J Cell Sci, 1981. 47: p. 167-85.
Holberton, D.V., "Fine structure of the ventral disk apparatus and the mechanism of attachment in the flagellate *Giardia muris*." J Cell Sci, 1973. 13(1): p. 11-41.
Holberton, D.V., "Mechanism of attachment of *Giardia* to the wall of the small intestine." Trans R Soc Trop Med Hyg, 1973. 67(1): p. 29-30.
Huang et al., "Biological Study of Naphthalene Derivatives with Antiinflammatory Activities," Drug Development Research, 60(4): 261-269 (2003).
Inge, P.M., C.M. Edson, and M.J. Farthing, "Attachment of *Giardia lamblia* to rat intestinal epithelial cells." Gut, 1988. 29(6): p. 795-801.
International Search Report & Written Opinion for PCT/US2010/058757; mailed Aug. 29, 2011; 12 pages.
Karanis, P., C. Kourenti, and H. Smith, "Waterborne transmission of protozoan parasites: a worldwide review of outbreaks and lessons learnt." J Water Health, 2007. 5(1): p. 1-38.
Katelaris, P.H. , A. Naeem, and M.J. Farthing, "Attachment of *Giardia lamblia* trophozoites to a cultured human intestinal cell line." Gut, 1995. 37(4): p. 512-8.
Kawasumi, M. and P. Nghiem, "Chemical genetics: elucidating biological systems with small-molecule compounds." J Invest Dermatol, 2007. 127(7): p. 1577-84.
Lane, S. and D. Lloyd, "Current trends in research into the waterborne parasite *Giardia*." Crit Rev Microbiol, 2002. 28 (2): p. 123-47.
Lengerich, E.J., A. D.G., and D.D. Juranek, "Severe giardiasis in the United States." Clin Infect Dis, 1994. 18(5): p. 760-763.
Liu, B., C.T. Archer, L. Burdine, T.G. Gillette, and T. Kodadek, "Label transfer chemistry for the characterization of protein-protein interactions." J Am Chem Soc, 2007. 129(41): p. 12348-9.
Ma, C., C. Li, L. Ganesan, J. Oak, S. Tsai, D. Sept, and N.S. Morrissette, "Mutations in {alpha}-Tubulin Confer Dinitroaniline Resistance at a Cost to Microtubule Function." Mol Biol Cell, 2007.
Magne, D., L. Favennec, C. Chochillon, A. Gorenflot, D. Meillet, N. Kapel, D. Raichvarg, J. Savel, and J.G. Gobert, "Role of cytoskeleton and surface lectins in *Giardia duodenalis* attachment to Caco2 cells." Parasitol Res, 1991. 77(8): p. 659-62.
Mital, J. and G.E. Ward, "Current and emerging approaches to studying invasion in apicomplexan parasites." Subcell Biochem, 2008. 47: p. 1-32.
Morrison, H.G., A.G. McArthur, F.D. Gillin, S.B. Aley, R.D. Adam, G.J. Olsen, A.A. Best, W.Z. Cande, F. Chen, M.J. Cipriano, B.J. Davids, S.C. Dawson, H.G. Elmendorf, A.B. Hehl, M.E. Holder, S.M. Huse, U.U. Kim, E. Lasek-Nesselquist, G. Manning, A. Nigam, J.E. Nixon, D. Palm, N.E. Passamaneck, A. Prabhu, C.I. Reich, D.S. Reiner, J. Samuelson, S.G. Svard, and M.L. Sogin, "Genomic minimalism in the early diverging intestinal parasite *Giardia lamblia*." Science, 2007. 317(5846): p. 1921-6.
Morrissette, N.S., A. Mitra, D. Sept, and L.D. Sibley, "Dinitroanilines bind alpha-tubulin to disrupt microtubules." Mol Biol Cell, 2004. 15(4): p. 1960-8.
Narcisi, E.M., J.J. Paulin, and M. Fechheimer, "Presence and localization of vinculin in *Giardia*." J Parasitol, 1994. 80 (3): p. 468-73.
Nayak, R.C., A.A. Sahasrabuddhe, V.K. Bajpai, and C.M. Gupta, "A novel homologue of coronin colocalizes with actin in filament-like structures in *Leishmania*." Mol Biochem Parasitol, 2005. 143(2): p. 152-64.
Ortega, Y.R. and R.D. Adam, "*Giardia*: overview and update." Clin Infect Dis, 1997. 25(3): p. 545-9; quiz 550.
Pattabiraman, N., "Analysis of ligand-macromolecule contacts: computational methods." Curr Med Chem, 2002. 9(5): p. 609-21.
Pattabiraman, N., "Occluded molecular surface analysis of ligand-macromolecule contacts: application to HIV-1 protease-inhibitor complexes." J Med Chem, 1999. 42(19): p. 3821-34.
Pattabiraman, N., H.M. Martinez, and B.A. Shapiro, "Molecular modeling and dynamics studies of HIV-1 kissing loop structures." J Biomol Struct Dyn, 2002. 20(3): p. 397-412.
Peterson, J.R., A.M. Lebensohn, H.E. Pelish, and M.W. Kirschner, "Biochemical suppression of small molecule inhibitors: a strategy to identify inhibitor targets and signaling pathway components." Chem Biol, 2006. 13(4): p. 443-52.
Rao, J. and N. Li, "Microfilament actin remodeling as a potential target for cancer drug development." Curr Cancer Drug Targets, 2004. 4(4): p. 345-54.
Roxstrom-Lindquist, K., D. Palm, D. Reiner, E. Ringqvist, and S.G. Svard, "*Giardia* immunity—an update." Trends Parasitol, 2006. 22(1): p. 26-31.
Sahasrabuddhe, A.A., V.K. Bajpai, and C.M. Gupta, "A novel form of actin in *Leishmania*: molecular characterisation, subcellular localisation and association with subpellicular microtubules." Mol Biochem Parasitol, 2004. 134(1): p. 105-14.
Sahoo, N., W. Beatty, J. Heuser, D. Sept, and L.D. Sibley, "Unusual kinetic and structural properties control rapid assembly and turnover of actin in the parasite *Toxoplasma gondii*." Mol Biol Cell, 2006. 17(2): p. 895-906.

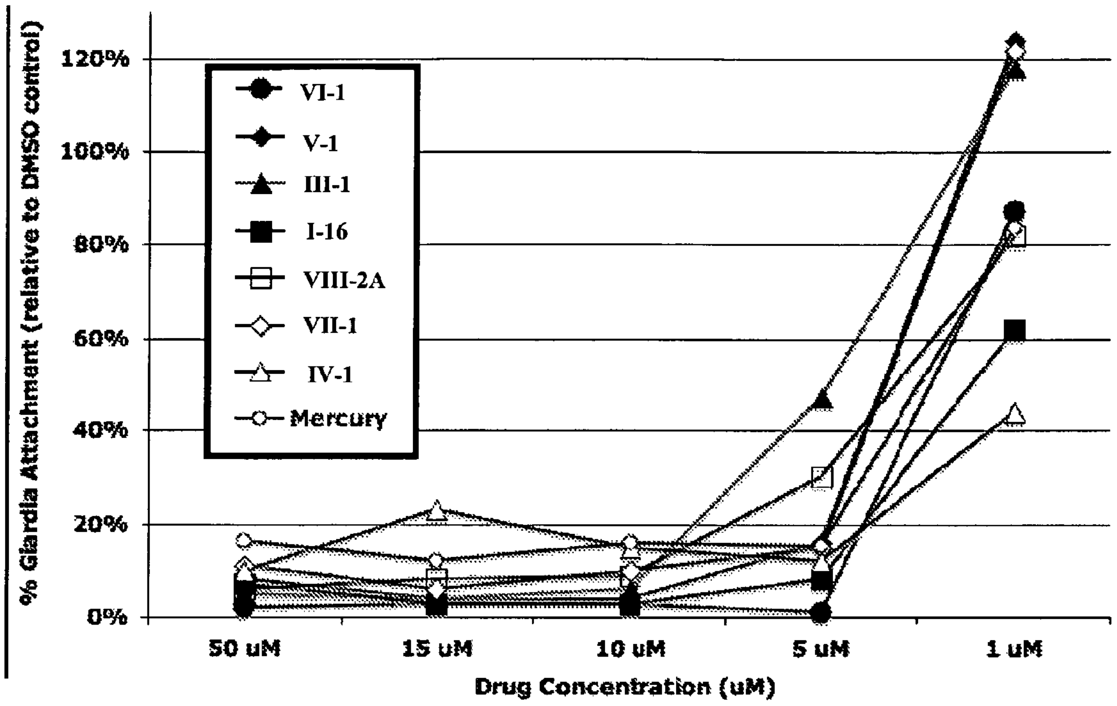
120%
100%
80%
60%
40%
20%
0%
% Giardia Attachment (relative to DMSO control)
VI-1
V-1
III-1
I-16
VIII-2A
VII-1
IV-1
Mercury
50 uM
15 uM
10 uM
5 uM
1 uM
Drug Concentration (uM)

COMPOSITIONS AND METHODS FOR THE TREATMENT OF GIARDIASIS

STATEMENT REGARDING FEDERALLY FUNDED RESEARCH

This invention was made with government support under Grant No. AI062934 awarded by the National Institutes of Health. The government has certain rights in the invention.

CROSS-REFERENCE TO PRIORITY APPLICATIONS

This application claims priority to U.S. Provisional Application No. 61/266,660, filed Dec. 4, 2009, which is incorporated herein by reference in its entirety.

BACKGROUND

*Giardia*, the most prevalent intestinal parasitic pathogen in humans and animals, is transmitted via contaminated food and water and is endemic in much of the world, resulting in estimates of 1 billion cases annually. In developed regions of the world, *Giardia* is primarily transmitted by a direct fecal-oral route, in freshwater supplies, and by occasional outbreaks from municipal water supplies, with estimates of from 500,000 to 2 million cases in the U.S. annually.

Infection results from ingestion of *Giardia* cysts that develop into trophozoites in response to the pH and enzyme environmental stresses present within the stomach. Within the small intestine, the trophozoites must attach to the intestinal wall to prevent expulsion by peristalsis and to initiate infection. This attachment is primarily mediated by a novel mechanical force, in contrast to the more typical receptor-ligand mechanism used by many pathogens. Despite research by several groups over the past four decades, remarkably little is understood about the processes by which *Giardia* parasites attach.

Infection can start with as few as 10 cysts, and an infected individual can release millions of cysts. Most infections are either asymptomatic or self-limiting, but a subset of individuals become chronically infected with weight loss and fail to thrive as a consequence. Symptoms include malabsorptive diarrhea, cramps, and flatulence. Both symptomatic and asymptomatic individuals transmit the parasite.

No vaccine is currently available for use, and disease control relies solely on a limited set of chemotherapeutic agents. In the U.S., clinically recognized cases are often treated with metronidazole, although this agent is not indicated for the treatment of giardiasis. Certain other nitroimidazoles, nitrofurans, and benzimidazoles can be used as secondary treatments.

While metronidazole is often effective, recurrence rates as high as 90% have been reported. Adverse reactions, including nausea, diarrhea, and/or metallic taste in the mouth, are also commonly reported. Some less common, but equally unpleasant, side effects are also associated with metronidazole administration. Most compounds, including metronidazole, require a relatively long period of administration (5-10 days), resulting in a low compliance rate. While shorter treatments are possible with certain agents, the incidence and severity of side effects typically then increases sharply. Furthermore, resistance to each of these drugs (up to 20% for metronidazole), and multi-drug resistance has been documented, and different parasite genotypes appear to have different drug sensitivities.

With limited treatment options, the unwanted side effects of currently used chemotherapeutic agents, parasite drug resistance, the number of incidences, and the high potential for transmission, giardiasis is a public health concern here and abroad. AIDS patients and pregnant women present particularly challenging treatment situations. Accordingly, there is a need to expand the limited repertoire of treatments for *Giardia* exposure and infection.

SUMMARY

Disclosed herein are compounds and methods for treating subjects infected with *Giardia lamblia* and/or suffering from giardiasis. Also disclosed herein are methods for antagonizing *Giardia lamblia* attachment to the intestinal wall of a subject. Such inhibition can occur, for example, by disrupting the parasite's morphology. The methods described herein include the use of compounds having one of at least seven general chemical formulas.

Compounds for treating or preventing giardiasis in a subject comprise compounds of the following formula:

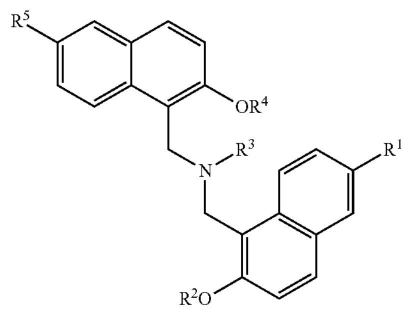

and include pharmaceutically acceptable salts or prodrugs thereof. In this class of molecules, $R^1$ and $R^5$ are each independently selected from hydrogen, cyano, and halogen; $R^2$ and $R^4$ are each independently selected from hydrogen, substituted or unsubstituted $C_1$-$C_6$ alkyl, and substituted or unsubstituted carbonyl; and $R^3$ is hydrogen, substituted or unsubstituted $C_1$-$C_6$ alkyl, or substituted or unsubstituted cycloalkyl. In this class of compounds, if $R^1$, $R^2$, $R^4$, and $R^5$ are simultaneously hydrogen, then $R^3$ is not hydrogen, methyl, n-butyl, cyclohexyl, phenyl, or benzyl. $R^3$ can be, for example, n-propyl, i-propyl, n-butyl, n-hexyl, or cyclohexyl. In some examples, $R^2$ and $R^4$ are each independently selected from hydrogen, methyl, and acetyl. Optionally, $R^1$ and $R^5$ are each independently selected hydrogen, cyano, and bromo.

Examples of these compounds include:

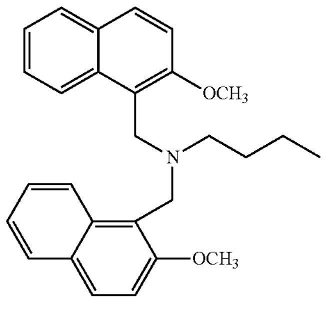

-continued
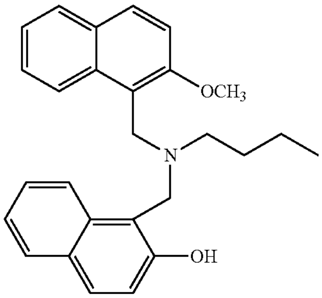
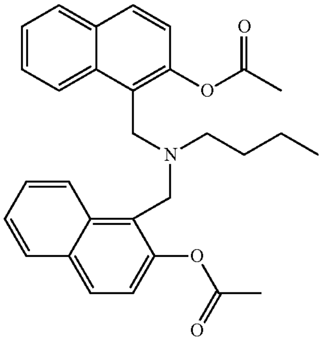
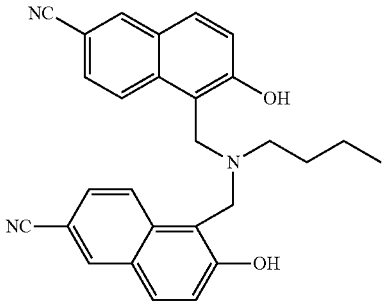
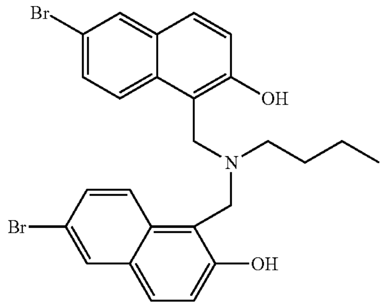
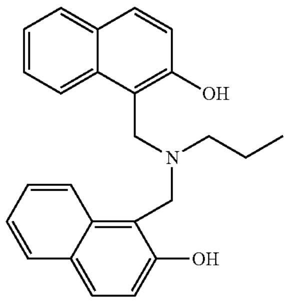
-continued
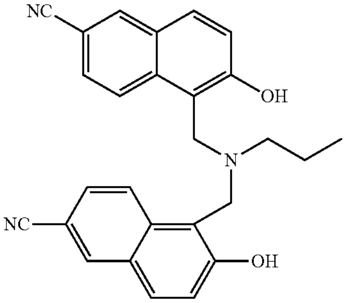
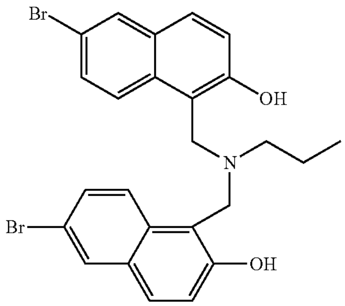
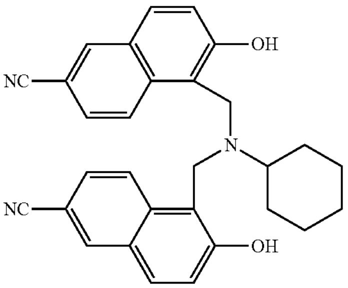
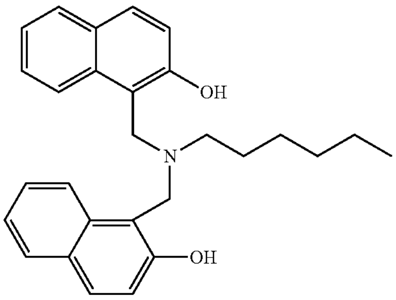
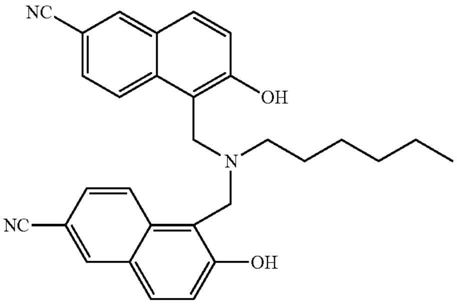

-continued

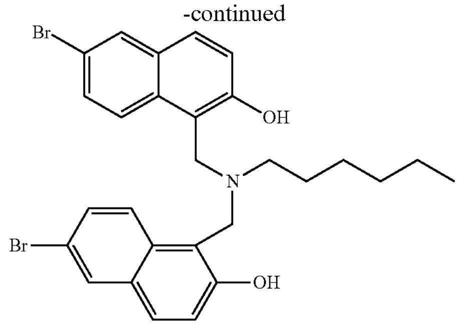

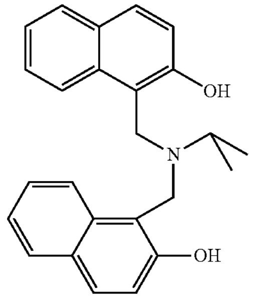

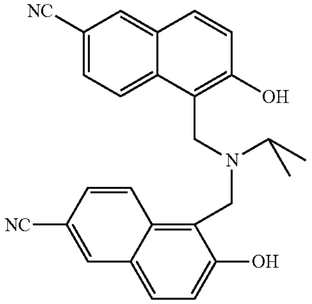

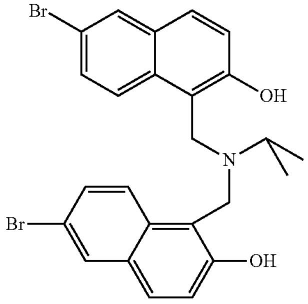

and pharmaceutically acceptable salts or prodrugs thereof.

Also described herein are compositions including a compound as described above and a pharmaceutically acceptable carrier.

Further provided herein are methods of treating or preventing giardiasis in a subject and/or antagonizing *Giardia lamblia* attachment to the intestinal wall of a subject. The methods optionally include administering to a subject a compound or composition as described above. Methods for treating or preventing giardiasis in a subject and/or antagonizing *Giardia lamblia* attachment to the intestinal wall of a subject include administering to the subject an effective amount of a compound of the following structure:

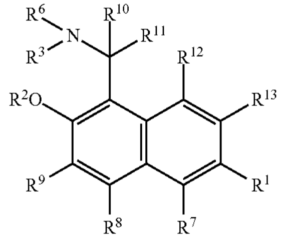

and pharmaceutically acceptable salts or prodrugs thereof, or a composition comprising the compound and a pharmaceutically acceptable carrier. In these methods, $R^1$ is hydrogen, cyano, or halogen; $R^2$ is hydrogen, substituted or unsubstituted $C_1$-$C_6$ alkyl, or substituted or unsubstituted carbonyl; $R^3$ and $R^6$ are each independently selected from hydrogen, substituted or unsubstituted $C_1$-$C_6$ alkyl, or substituted or unsubstituted cycloalkyl; and $R^7$, $R^8$, $R^9$, $R^{10}$, $R^{11}$, $R^{12}$, and $R^{13}$ are each independently selected from hydrogen, halogen, hydroxyl, cyano, nitro, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, or substituted or unsubstituted carboxyl. $R^6$ can be, for example, t-butyl, substituted methyl (e.g., methyl substituted with a substituted or unsubstituted naphthyl), or the following structure

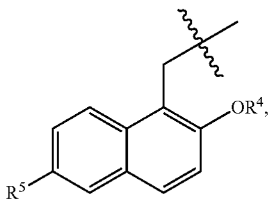

wherein $R^4$ is hydrogen, substituted or unsubstituted $C_1$-$C_6$ alkyl, or substituted or unsubstituted carbonyl; and $R^5$ is hydrogen, cyano, or halogen. Examples of compounds useful for these methods include

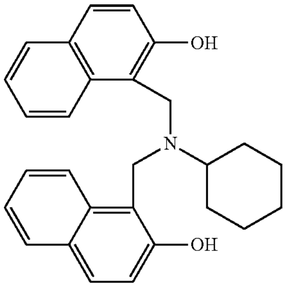

,

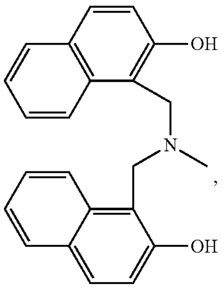

,

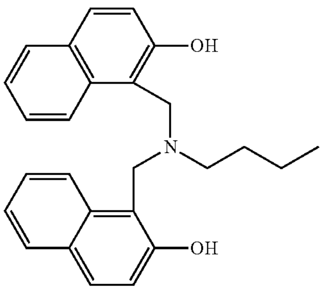

,

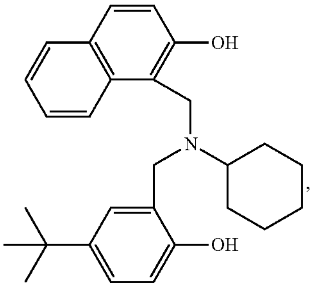

,

-continued

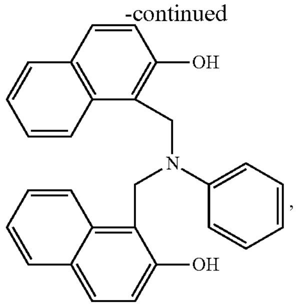

, and

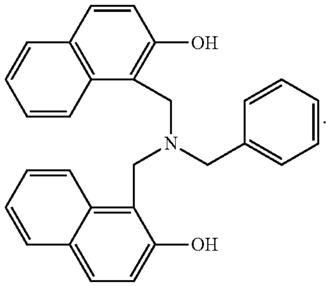

Methods for treating or preventing giardiasis in a subject and/or antagonizing *Giardia lamblia* attachment to the intestinal wall of a subject optionally include administering to the subject an effective amount of a compound of the following structure:

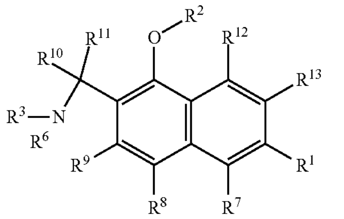

and pharmaceutically acceptable salts or prodrugs thereof, or a composition comprising the compound and a pharmaceutically acceptable carrier. In these methods, $R^1$ is hydrogen, cyano, or halogen; $R^2$ is hydrogen, substituted or unsubstituted $C_1$-$C_6$ alkyl, or substituted or unsubstituted carbonyl; $R^3$ and $R^6$ are each independently selected from hydrogen, substituted or unsubstituted $C_1$-$C_6$ alkyl, or substituted or unsubstituted cycloalkyl; and $R^7$, $R^8$, $R^9$, $R^{10}$, $R^{11}$, $R^{12}$, and $R^{13}$ are each independently selected from hydrogen, halogen, hydroxyl, cyano, nitro, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, or substituted or unsubstituted carboxyl. In some examples, $R^3$ and $R^6$ combine to form a substituted or unsubstituted heterocycloalkyl. Examples of compounds useful for these methods include

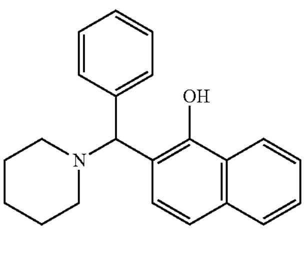

and

-continued

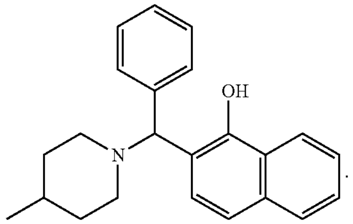

Methods for treating or preventing giardiasis in a subject and/or antagonizing *Giardia lamblia* attachment to the intestinal wall of a subject include administering to the subject an effective amount of a compound of the following structure:

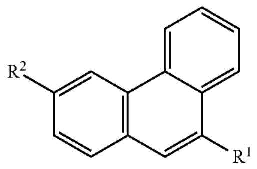

and pharmaceutically acceptable salts or prodrugs thereof, or a composition comprising the compound and a pharmaceutically acceptable carrier. In these methods, $R^1$ is halogen; and $R^2$ is substituted or unsubstituted carbonyl. An example of a compound useful for these methods includes

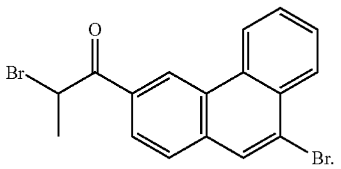 [SMILES: CC(Br)C(=O)c1ccc2cc(Br)c3ccccc3c2c1]

Methods for treating or preventing giardiasis in a subject and/or antagonizing *Giardia lamblia* attachment to the intestinal wall of a subject include administering to the subject an effective amount of a compound of the following structure:

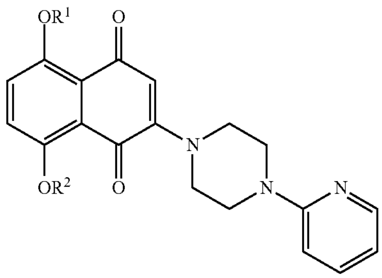

and pharmaceutically acceptable salts or prodrugs thereof, or a composition comprising the compound and a pharmaceutically acceptable carrier. In these methods, $R^1$ and $R^2$ are each independently selected from hydrogen, substituted or unsubstituted $C_1$-$C_6$ alkyl, or substituted or unsubstituted carbonyl. An example of a compound useful for these methods includes

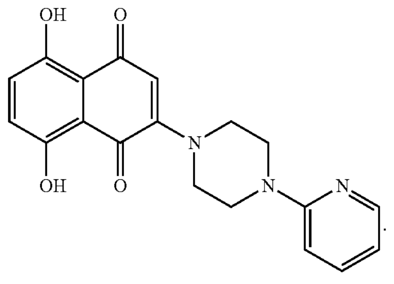 [SMILES: O=C1C=C(N2CCN(c3ccccn3)CC2)C(=O)c2c(O)ccc(O)c21]

Methods for treating or preventing giardiasis in a subject and/or antagonizing *Giardia lamblia* attachment to the intestinal wall of a subject include administering to the subject an effective amount of a compound of the following structure:

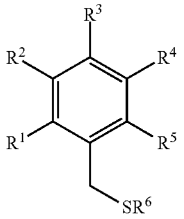

and pharmaceutically acceptable salts or prodrugs thereof, or a composition comprising the compound and a pharmaceutically acceptable carrier. In these methods, $R^1$, $R^2$, $R^3$, $R^4$, and $R^5$ are each independently selected from hydrogen, halogen, hydroxyl, cyano, nitro, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, or substituted or unsubstituted carboxyl; and $R^6$ is a substituted or unsubstituted heterocycle. In some examples, $R^6$ is a purine. Examples of compounds useful for these methods include

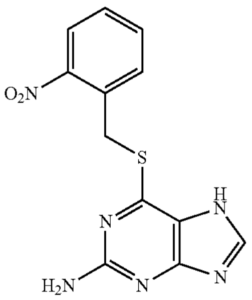

and

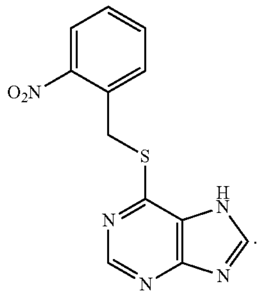

Methods for treating or preventing giardiasis in a subject and/or antagonizing *Giardia lamblia* attachment to the intestinal wall of a subject include administering to the subject an effective amount of a compound of the following structure:

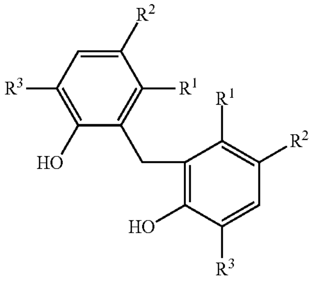

and pharmaceutically acceptable salts or prodrug thereof, or a composition comprising the compound and a pharmaceutically acceptable carrier. In these methods, $R^1$ and $R^3$ are each independently a substituted or unsubstituted $C_1$-$C_6$ alkyl; and $R^2$ is halogen. An example of a compound useful for these methods includes

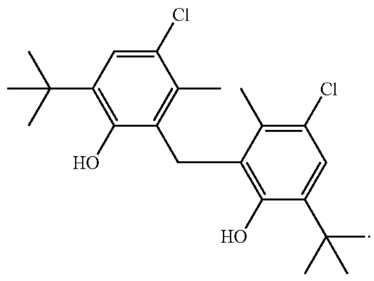

Methods of treating or preventing giardiasis in a subject and/or antagonizing *Giardia lamblia* attachment to the intestinal wall of a subject further include administering to the subject an effective amount of a compound of the following structure:

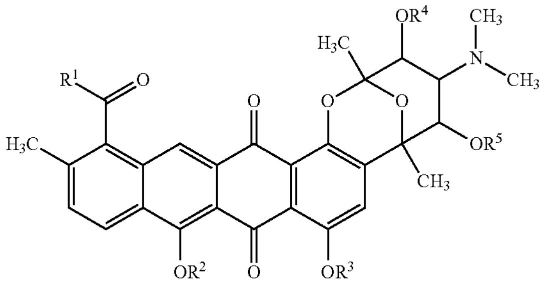

and pharmaceutically acceptable salts or prodrugs thereof, or a composition comprising the compound and a pharmaceutically acceptable carrier. In these methods, $R^1$ is hydrogen, substituted or unsubstituted $C_1$-$C_6$ alkyl, or substituted or unsubstituted alkoxyl; and $R^2$, $R^2$, $R^4$, and $R^5$ are each independently selected from hydrogen and substituted or unsubstituted $C_1$-$C_6$ alkyl. An example of a compound useful for these methods includes

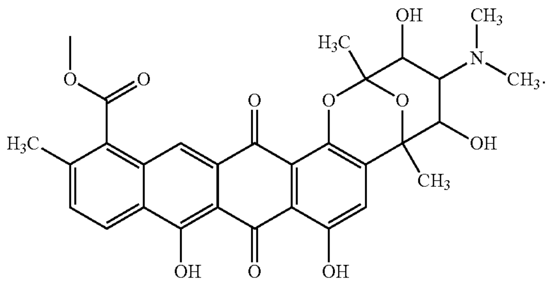

Methods of treating or preventing giardiasis in a subject and/or antagonizing *Giardia lamblia* attachment to the intestinal wall of a subject include administering to the subject an effective amount of a compound of the following structure:

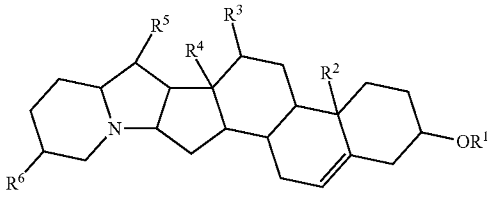

and pharmaceutically acceptable salts or prodrugs thereof, or a composition comprising the compound and a pharmaceutically acceptable carrier. In these methods, $R^1$ is hydrogen or substituted or unsubstituted $C_1$-$C_6$ alkyl; and $R^2$, $R^3$, $R^4$, $R^5$, and $R^6$ are each independently selected from hydrogen, substituted or unsubstituted $C_1$-$C_6$ alkyl, or substituted or unsubstituted alkoxyl. Examples of compounds useful for these methods include

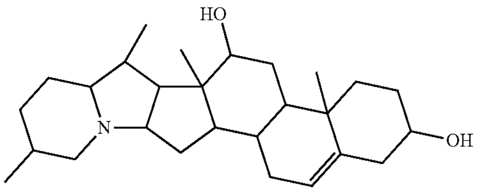

and

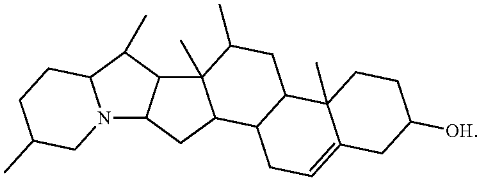

The details of one or more embodiments are set forth in the description below. Other features, objects, and advantages are apparent from the drawings, from the description, and from the claims.

DESCRIPTION OF THE DRAWINGS

FIG. 1 shows the dose-dependent effect of Compound III-1, Compound IV-1, Compound V-1, Compound VI-1, Compound VII-1, Compound I-16, and Compound VIII-2A on the attachment of *Giardia* to polystyrene microplates. Mercury was used as the control.

DETAILED DESCRIPTION

The compounds and methods disclosed herein are useful for treating and preventing giardiasis in a subject. For example, the compounds and methods described herein are useful for treating, ameliorating, and preventing symptoms associated with exposure to *Giardia lamblia* and giardiasis. Such symptoms are known in the art to include malabsorptive diarrhea, cramps, flatulence, anorexia, malaise, and fatigue. Such use entails delivering one or more of the compounds to the affected or at-risk cells of a subject afflicted with, suspected of being afflicted with, or at risk for developing giardiasis. Such delivery can be achieved by any of a variety of routes, such as oral administration of a solid or liquid composition including the compound, by injection of a composition including the compound, or by local implantation of a sustained-release composition including the compound.

I. DEFINITIONS

Unless otherwise defined, all technical and scientific terms used herein have the same meaning as commonly understood by one of ordinary skill in the art. Although methods and materials similar or equivalent to those described herein can be used in the practice or testing of the described embodiments, suitable methods and materials are described below. All publications, patent applications, patents, and other references mentioned herein are incorporated by reference in their entirety. In case of conflict, the present specification, including definitions, will control. As used herein, the singular forms "a," "an," and "the" include plural referents unless the context clearly dictates otherwise.

As used herein, "administering" or "administration" refers to delivery of a compound described herein by any external route, including, without limitation, intravenous, intramuscular, subcutaneous, intranasal, inhalation, transdermal, oral, rectal, sublingual, and parenteral administration.

The term "contacting" refers to bringing at least two moieties together, whether in an in vitro system or an in vivo system.

The expression "effective amount," when used to describe an amount of compound applied in a method, refers to the amount of a compound that achieves the desired pharmacological effect or other effect, for example an amount that slows attachment to *Giardia lamblia*, resulting in a useful effect.

As used herein the terms "treatment," "treat," or "treating" refer to a method of reducing the effects of a disease or condition or symptom of the disease or condition. Thus in the disclosed method, treatment can refer to a 10%, 20%, 30%, 40%, 50%, 60%, 70%, 80%, 90%, or 100% reduction in the severity of an established disease or condition or one or more symptoms of the disease or condition. For example, a method for treating a disease is considered to be a treatment if there is a 10% reduction in one or more symptoms or signs (e.g., size of the tumor or rate of tumor growth) of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms "prevent," "preventing," and "prevention" of a disease or disorder refer to an action, for example, administration of a composition or therapeutic agent, that occurs before or at about the same time a subject begins to show one or more symptoms of the disease or disorder, which inhibits or delays onset or severity of one or more symptoms of the disease or disorder. As used herein, references to "decreasing," "reducing," or "inhibiting" include a change of 10%, 20%, 30%, 40%, 50%, 60%, 70%, 80%, 90% or greater as compared to a control level. Such terms can include but do not necessarily include complete elimination.

As used herein, "subject" means both mammals and non-mammals. Mammals include, for example, humans; non-human primates, e.g. apes and monkeys; cattle; horses; sheep; rats; mice; pigs; and goats. Non-mammals include, for example, fish and birds.

The term "alkyl," by itself or as part of another substituent, means, unless otherwise stated, a straight or branched chain, which may be fully saturated, mono- or polyunsaturated, can include di- and multivalent radicals, and can have a number of carbon atoms optionally designated (i.e., $C_1$-$C_6$ means one to six carbons). Examples of saturated hydrocarbon groups include, but are not limited to, groups such as methyl, ethyl, n-propyl, isopropyl, n-butyl, t-butyl, isobutyl, sec-butyl, n-pentyl, isopentyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotonyl, 2-isopentenyl, 2-(butadienyl), 2,4-pentadienyl, 3-(1,4-pentadienyl), ethynyl, 1- and 3-propynyl, 3-butyryl, and higher homologs and isomers.

The term "alkoxy" refers to those alkyl groups attached to the remainder of the molecule via an oxygen atom. Alkoxy groups include, but are not limited to, methoxy, ethoxy, isopropoxy, trifluoromethoxy, and difluoromethoxy.

The term "cycloalkyl", by itself or in combination with other terms, represents, unless otherwise stated, cyclic versions of substituted or unsubstituted "alkyl". Examples of cycloalkyl groups include, but are not limited to, cyclopentyl, cyclohexyl, 1-cyclohexenyl, 3-cyclohexenyl, cycloheptyl, and the like. The carbon atoms of the cyclic structures are optionally oxidized.

The term "heterocycloalkyl" as used herein refers to a cycloalkyl having a heteroatom. The heteroatom can occupy any position, including the position at which the heterocycle is attached to the remainder of the molecule. Examples of heterocycloalkyl groups include, but are not limited to, pyrrolidinyl, 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, dihydroimidazolyl, benzoimidazolyl, dihydrooxazolyl, and the like. The heteroatoms and carbon atoms of the cyclic structures are optionally oxidized or, in the case of N, quaternized.

The terms "halo" or "halogen," by themselves or as part of another substituent, refer to, unless otherwise stated, a fluorine, chlorine, bromine, or iodine atom.

The term "aryl" refers to, unless otherwise stated, a polyunsaturated, aromatic, hydrocarbon moiety which can be a single ring or multiple rings (e.g., from 1 to 3 rings) which are fused together or linked covalently. The term "heteroaryl" refers to aryl groups (or rings) that contain from one to four heteroatoms selected from N, O, and S, wherein the nitrogen, carbon, and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. "Aryl" and "heteroaryl" also encompass ring systems in which one or more non-aromatic ring systems are fused, or otherwise bound, to an aryl or heteroaryl system. Aryl-containing groups include, but are not limited to, phenyl, phenoxycarbonyl, benzoyl, benzyl, phenylpiperidinyl, phenylmorpholinyl, and dihydrobenzodioxyl (e.g., N,N-dihydrobenzodioxyl).

As used herein, "substituted" or "optionally substituted" refers to substitution by one or more substituents (e.g., one, two, three, or four substituents). In some embodiments, two substituents may join to form a cyclic or heterocyclic ring containing 3-7 atoms. Non-limiting examples of substituents include $C_{1-10}$ alkyl; $OR^1$; halo; $NR^1R^2$; $NO_2$; CN; $SR^1$; $SO_2$; $COOR^1$; $C_{5-12}$ cycloalkyl; $C_{5-12}$ heterocycloalkyl; $C_{5-12}$ aryl; and $C_{5-12}$ heteroaryl; wherein the alkyl, cycloalkyl, heterocycloalkyl, aryl, or heteroaryl may be substituted or unsubstituted, wherein each $R^1$ and $R^2$ is independently H or $C_{1-10}$ substituted or unsubstituted alkyl. In some embodiments, a substituent is selected from $C_{1-6}$ alkyl, halo, and $OR^1$.

As used herein, the term "heteroatom" includes oxygen (O), nitrogen (N), or sulfur (S).

II. COMPOUNDS

The compounds described herein and pharmaceutically acceptable salts and prodrugs thereof are useful for treating and preventing giardiasis in a subject. Specifically, the compounds are useful for the chemotherapeutic antagonization of *Giardia lamblia* infection. For example, the compounds are useful for antagonizing *Giardia lamblia* attachment to the intestinal wall of a subject. Such antagonization or inhibition can occur, for example, by disrupting the parasite's morphology.

A first group of inhibitors includes compounds represented by Formula I:

(I)

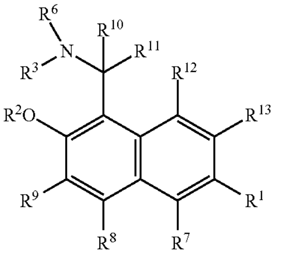

and pharmaceutically acceptable salts and prodrugs thereof.

In Formula I, $R^1$ is hydrogen, cyano, or halogen.

Also in Formula I, $R^2$ is hydrogen, substituted or unsubstituted $C_1$-$C_6$ alkyl, or substituted or unsubstituted carbonyl.

Additionally in Formula I, $R^3$ and $R^6$ are each independently selected from hydrogen, substituted or unsubstituted $C_1$-$C_6$ alkyl, or substituted or unsubstituted cycloalkyl. In some examples, $R^6$ is t-butyl or substituted methyl. For example, $R^6$ can be a methyl group substituted with a substituted or unsubstituted naphthyl group as shown below:

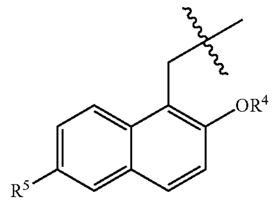

$R^4$ is hydrogen, substituted or unsubstituted $C_1$-$C_6$ alkyl, or substituted or unsubstituted carbonyl and $R^5$ is hydrogen, cyano, or halogen.

Further in Formula I, $R^7$, $R^8$, $R^9$, $R^{10}$, $R^{11}$, $R^{12}$, and $R^{13}$ are each independently selected from hydrogen, halogen, hydroxyl, cyano, nitro, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, or substituted or unsubstituted carboxyl.

Examples of Formula I include compounds represented by Formula I-A:

(I-A)

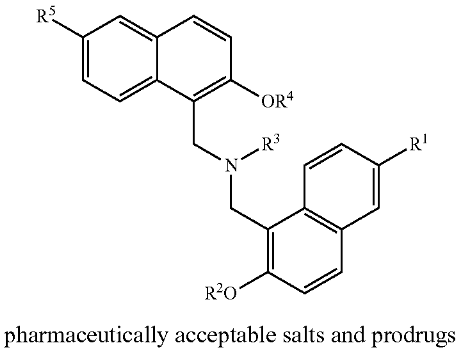

and pharmaceutically acceptable salts and prodrugs thereof.

In Formula I-A, $R^1$ and $R^5$ are each independently selected from hydrogen, cyano, and halogen. In some examples, $R^1$ and $R^5$ are each independently selected from hydrogen, cyano, and bromo.

Also in Formula I-A, $R^2$ and $R^4$ are each independently selected from hydrogen, substituted or unsubstituted $C_1$-$C_6$ alkyl, and substituted or unsubstituted carbonyl. In some examples, $R^2$ and $R^4$ are each independently selected from hydrogen, methyl, and acetyl.

Additionally in Formula I-A, $R^3$ is hydrogen, substituted or unsubstituted $C_6$ alkyl, or substituted or unsubstituted cycloalkyl. In some examples, $R^3$ is methyl, n-propyl, i-propyl, n-butyl, n-hexyl, cyclohexyl, or phenyl.

In some examples of Formula I-A, if $R^1$, $R^2$, $R^4$, and $R^5$ are simultaneously hydrogen, then $R^3$ is not hydrogen, methyl, n-butyl, cyclohexyl, phenyl, or benzyl.

Particular examples of Formula I include the following compounds:

Compound I-1

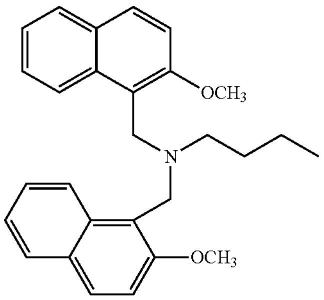

Compound I-2

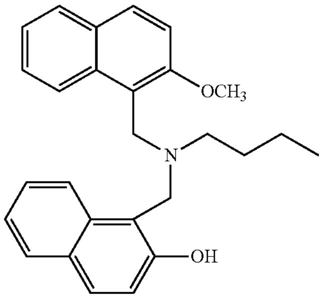

Compound I-3

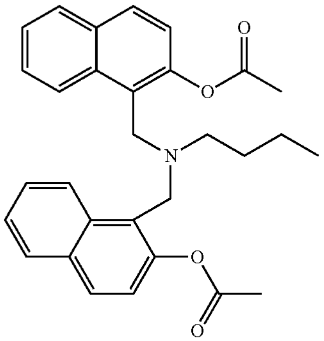

-continued

Compound I-4

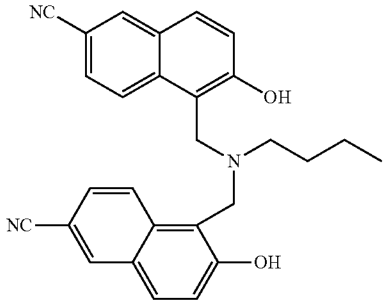

Compound I-5

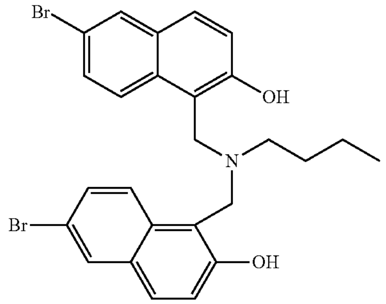

Compound I-6

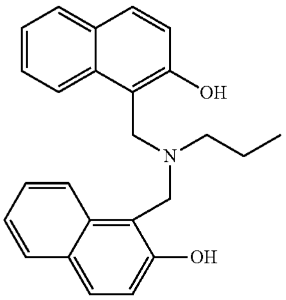

Compound I-7

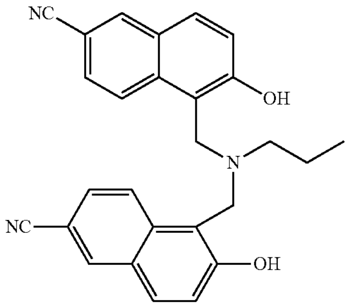

Compound I-8

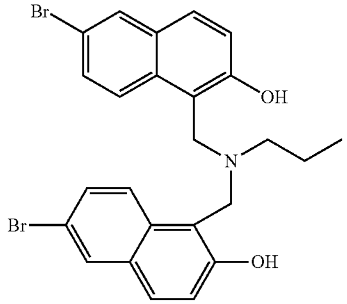

-continued
Compound I-9
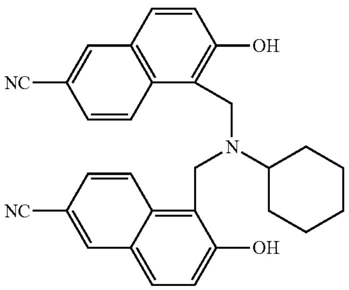
Compound I-10
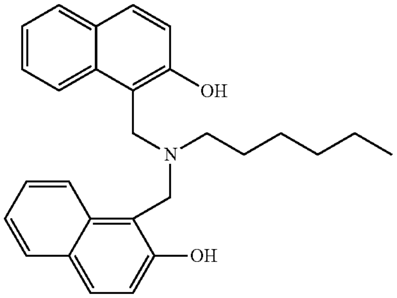
Compound I-11
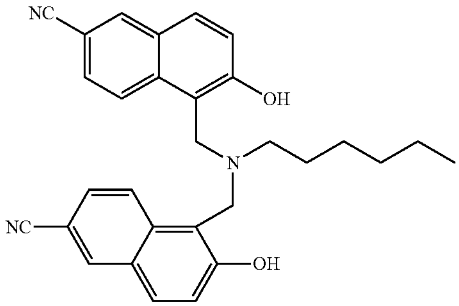
Compound I-12
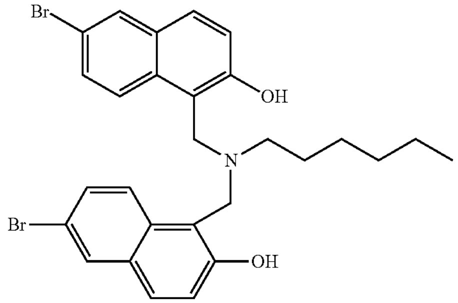
Compound I-13
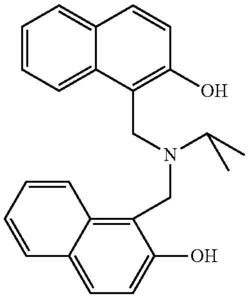
-continued
Compound I-14
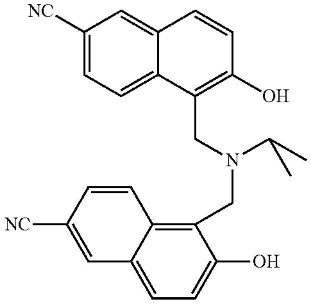
Compound I-15
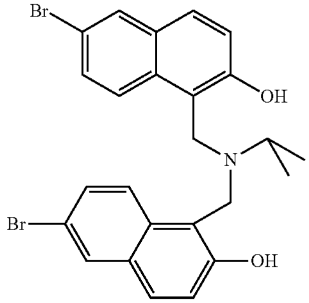
Compound I-16
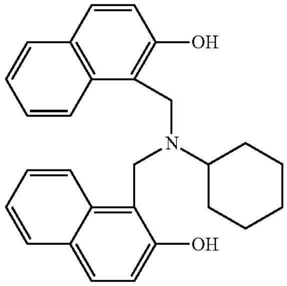
(NSC47949)
Compound I-17
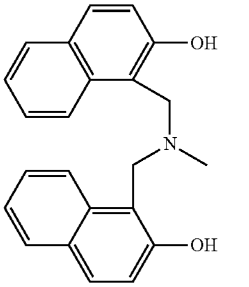
(NSC47941)
Compound I-18
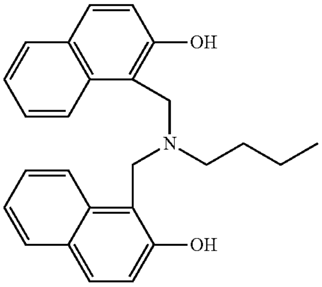
(NSC47947)

-continued

Compound I-19

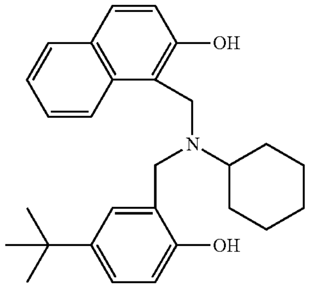

(NSC48858)

Compound I-20

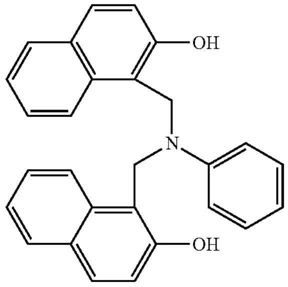

(NSC48869)

Compound I-21

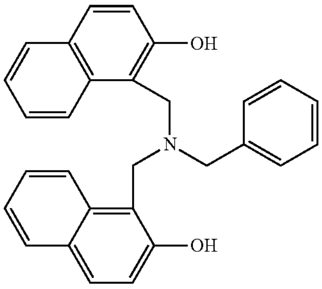

(NSC47950)

Compouind I-22

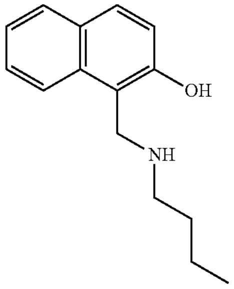

In some examples of Formula I, the compound is not Compound I-16, Compound I-17, Compound I-18, Compound I-19, Compound I-20, Compound I-21, or Compound I-22. Optionally, the compounds can be an acid salt of the compound (e.g., the HCl salt of the compound). Optionally, the compound can be in a free base form.

A second group of inhibitors includes compounds represented by Formula II:

(II)

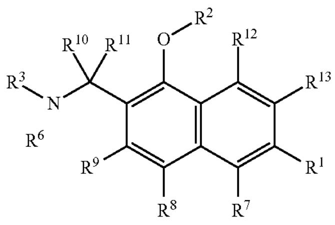

and pharmaceutically acceptable salts and prodrugs thereof.

In Formula II, $R^1$ is hydrogen, cyano, or halogen.

Also in Formula II, $R^2$ is hydrogen, substituted or unsubstituted $C_1$-$C_6$ alkyl, or substituted or unsubstituted carbonyl.

Additionally in Formula II, $R^3$ and $R^6$ are each independently selected from hydrogen, substituted or unsubstituted $C_1$-$C_6$ alkyl, or substituted or unsubstituted cycloalkyl. Optionally, $R^3$ and $R^6$ can combine to form a substituted or unsubstituted heterocycloalkyl.

Further in Formula II, $R^7$, $R^8$, $R^9$, $R^{10}$, $R^{11}$, $R^{12}$, and $R^{13}$ are each independently selected from hydrogen, halogen, hydroxyl, cyano, nitro, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, or substituted or unsubstituted carboxyl.

Particular examples of Formula II include the compounds shown below:

Compound II-1

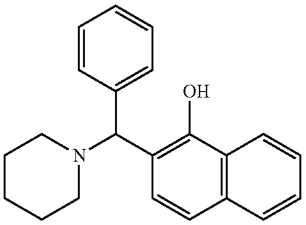

(NCS150235)

Compound II-2

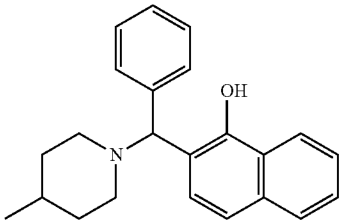

(NCS147991)

In some examples of Formula II, the compound is not Compound II-1 or Compound II-2.

A third group of inhibitors includes halophenanthrenyl propanone compounds and derivatives. The halophenanthrenyl propanone compounds described herein can include compounds represented by Formula III:

(III)

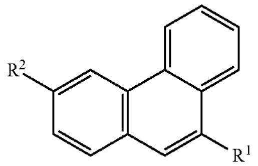

and pharmaceutically acceptable salts and prodrugs thereof.

In Formula III, $R^1$ is a halogen. In some examples, $R^1$ is bromo.

Also in Formula III, $R^2$ is substituted or unsubstituted carbonyl.

In some examples, the halophenanthrenyl propanone compounds can be bromophenanthrenyl propanone compounds. A particular example of Formula III includes the compound shown below:

Compound III-1

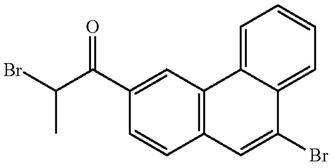

(NSC44480)

Suitable derivatives of the halophenanthrenyl propanone compounds can include compounds of Formula III where one or more hydrogen atoms are independently substituted by one or more halo, alkyl, cycloalkyl, alkoxyl, aryl, aryloxyl, alkenyl, and alkynyl groups. In some examples, the compound of Formula III is not Compound III-1.

A fourth group of inhibitors includes pyridinyl-piperazinyl naphthalenedione compounds and derivatives. The pyridinyl-piperazinyl naphthalenedione compounds described herein can include compounds represented by Formula IV:

(IV)

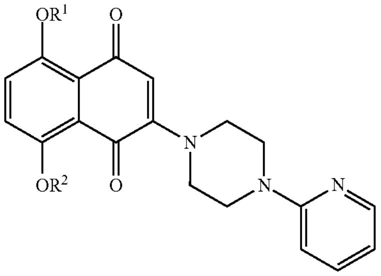

and pharmaceutically acceptable salts and prodrugs thereof.

In Formula IV, $R^1$ and $R^2$ are each independently selected from hydrogen, substituted or unsubstituted $C_1$-$C_6$ alkyl, or substituted or unsubstituted carbonyl. In some examples, the pyridinyl-piperazinyl naphthalenedione compounds can be hydroxy-pyridinyl-piperazinyl naphthalenedione compounds. A particular example of Formula IV includes the compound shown below:

Compound IV-1

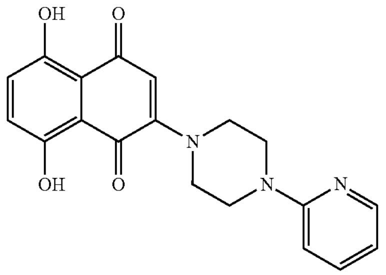

(NSC658142)

Suitable derivatives of the pyridinyl-piperazinyl naphthalenedione derivatives can include compounds of Formula IV where one or more hydrogen atoms are independently substituted by one or more halo, alkyl, cycloalkyl, alkoxyl, aryl, aryloxyl, alkenyl, and alkynyl groups. In some examples, the compound of Formula IV is not Compound IV-1.

A fifth group of inhibitors includes phenyl methylsulfanyl amine compounds and derivatives. The phenyl methylsulfanyl amine compounds described herein can include compounds represented by Formula V:

(V)

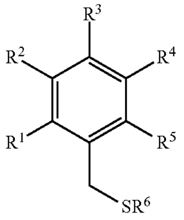

and pharmaceutically acceptable salts and prodrugs thereof.

In Formula V, $R^1$, $R^2$, $R^3$, $R^4$, and $R^5$ are each independently selected from hydrogen, halogen, hydroxyl, cyano, nitro, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, or substituted or unsubstituted carboxyl.

Also in Formula V, $R^6$ is a substituted or unsubstituted heterocycle. In some examples, $R^6$ is a purine. In some examples, the phenyl methylsulfanyl amine compounds can be nitrophenyl methylsulfanyl purine amine compounds. Particular examples of Formula V include the compounds shown below:

Compound V-1

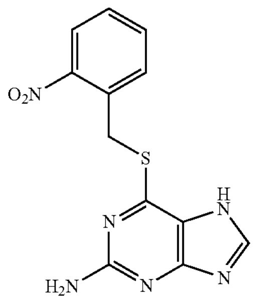

(NSC38737)

-continued

Compound V-2

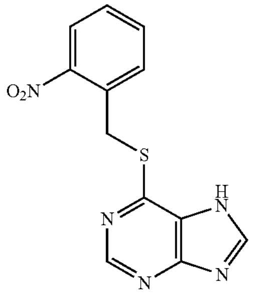

(NSC39334)

Suitable derivatives of the phenyl methylsulfanyl amine compounds can include compounds of Formula V where one or more hydrogen atoms are independently substituted by one or more halo, alkyl, cycloalkyl, alkoxyl, aryl, aryloxyl, alkenyl, and alkynyl groups. In some examples, the compound of Formula V is not Compound V-1 or Compound V-2.

A sixth group of inhibitors includes bis-phenol compounds and derivatives as represented by Formula VI:

(VI)

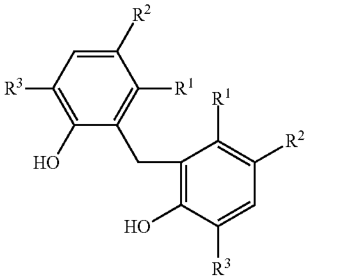

In Formula VI, $R^1$ and $R^3$ are each independently a substituted or unsubstituted $C_1$-$C_6$ alkyl.

Also in Formula VI, $R^2$ is halogen. In some examples, $R^2$ is chloro.

Particular examples of Formula VI include methane-bis-methyl-t-butylchlorophenol compounds and derivatives, such as the compound shown below:

Compound VI-1

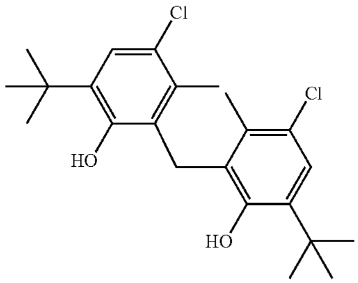

(NSC5857)

Suitable derivatives of the methane-bis-methyl-t-butylchlorophenol compounds can include derivatives of Compound VI-1 where one or more chlorine atoms are substituted by an alternative halogen (e.g., bromo or fluoro). Further examples of suitable derivatives of Compound VI-1 can include those where one or more hydrogen atoms are independently substituted by one or more halo, alkyl, cycloalkyl, alkoxyl, aryl, aryloxyl, alkenyl, and alkynyl groups. In some examples, the compound of Formula VI is not Compound VI-1.

A seventh group of inhibitors includes Nogalamycin and related compounds as represented by Formula VII:

(VII)

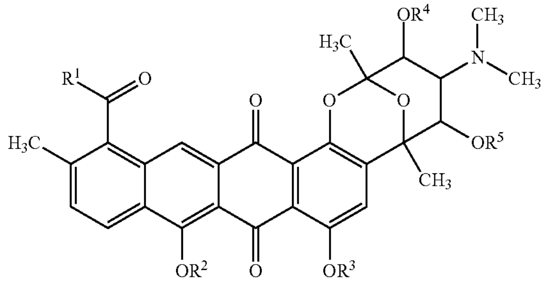

In Formula VII, $R^1$ is hydrogen, substituted or unsubstituted $C_1$-$C_6$ alkyl, or substituted or unsubstituted alkoxyl.

Also in Formula VII, $R^2$, $R^2$, $R^4$, and $R^5$ are each independently selected from hydrogen and substituted or unsubstituted $C_1$-$C_6$ alkyl.

A particular example of Formula VII includes Nogalamycin (Compound VII-1) as shown below.

Compound VII-1

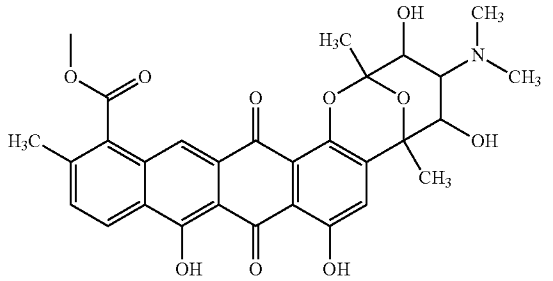

(NSC82892)

Suitable derivatives of Formula VII can include those where one or more hydrogen atoms are independently substituted by one or more halo, alkyl, cycloalkyl, alkoxyl, aryl, aryloxyl, alkenyl, and alkynyl groups. In some examples, the compound of Formula VII is not Nogalamycin (Compound VII-1).

An eighth group of inhibitors includes Rubigervine and related compounds as represented by Formula VIII:

(VIII)

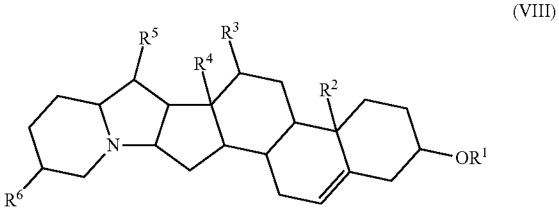

In Formula VIII, $R^1$ is hydrogen or substituted or unsubstituted $C_1$-$C_6$ alkyl.

Also in Formula VIII, $R^2$, $R^3$, $R^4$, $R^5$, and $R^6$ are each independently selected from hydrogen, substituted or unsubstituted $C_1$-$C_6$ alkyl, or substituted or unsubstituted alkoxyl.

Particular examples of Formula VIII include the compounds shown below.

Compound VIII-1

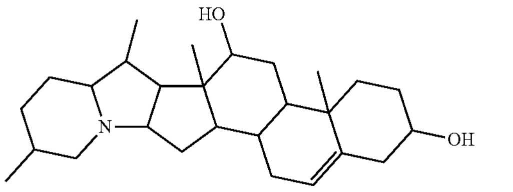

Compound VIII-2

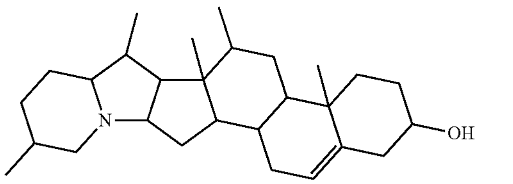

In some examples, Compound VIII-1 can be Compound VIII-1A. In some examples, Compound VIII-2 can be Compound VIII-2A.

Compound VIII-1A

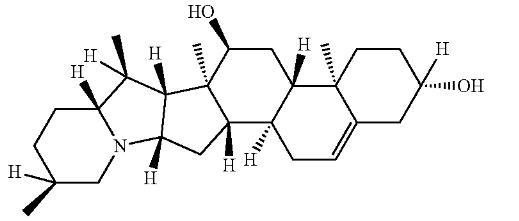

(NSC76026)

Compound VIII-2A

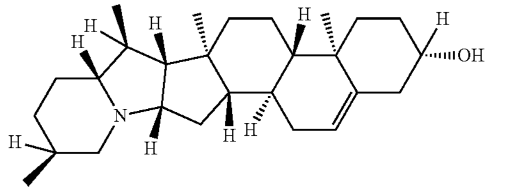

(NSC76025)

Suitable derivatives of Formula VIII can include those where one or more hydrogen atoms are independently substituted by one or more halo, alkyl, cycloalkyl, alkoxyl, aryl, aryloxyl, alkenyl, and alkynyl groups. In some examples, the compound of Formula VIII is not Compound VIII-1A or Compound VIII-2A.

III. PHARMACEUTICAL FORMULATIONS

The compounds described herein or derivatives thereof can be formulated as pharmaceutically acceptable salts. Pharmaceutically acceptable salts are well known in the art and refer to derivatives of the disclosed compounds that include acid or base cations or salts.

Pharmaceutically acceptable salts can include sulfate, pyrosulfate, bisulfate, sulfite, bisulfite, phosphate, ammonium, monohydrogen phosphate, dihydrogen phosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, furmarate, hippurate, maleate, butyne-1,4-dioate, hexyne-1,6-dioate, benzoate, chlorobenzoate, methylbenzoate, dinitrobenzoate, hydroxylbenzoate, methoxybenzoate, phthalate, sulfonate, xylenesulfonate, phenylacetate, phenylpropionate, phenylbutyrate, citrate, lactate, α-hydroxybutyrate, glycolate, maleate, tartrate, methanesulfonate, propanesulfonate, naphthalene-1-sulfonate, napthalene-2-sulfonate, mandelate, magnesium, tetramethylammonium, potassium, trimethylammonium, sodium, methylammonium, calcium, and like salts. Lists of suitable salts are found in, for example, Remington, 2006, *The Science and Practice of Pharmacy,* 21st Edition, Lippincott Williams & Wilkins.

Optionally, the compounds described herein can be formulated as pharmaceutically acceptable hydrates or solvates.

The compounds disclosed herein can be formulated as a pharmaceutical composition comprising one or more of the compounds described herein together with a pharmaceutically acceptable carrier. Suitable pharmaceutical carriers are described, for example, in Remington: *The Science and Practice of Pharmacy,* 21st Edition (Lippincott Williams & Wilkins, 2006). Pharmaceutically acceptable carriers can be sterile liquids, such as water and oils, including those of petroleum, animal, vegetable or synthetic origin, such as peanut oil, soybean oil, mineral oil, and sesame oil. In particular embodiments, water-based solutions are advantageous carriers, such as when the pharmaceutical composition is administered intravenously. For example, saline solutions, aqueous dextrose, and glycerol solutions are advantageous in certain embodiments, particularly for injectable solutions. If a particular antagonist exhibits relatively low solubility in aqueous systems, any of a wide variety of alternative pharmaceutically acceptable solvents and additives are known that can improve the solubility of the antagonist in the vehicle desired for delivery. By way of example, the antagonist can be dissolved and/or suspended in an alcohol (e.g., ethanol) solution or in a composition including DMSO or a detergent.

In addition to the pharmacologically active agent, the pharmaceutical compositions described herein can include suitable pharmaceutically acceptable carriers, such as those comprising excipients and auxiliaries to facilitate processing of the active compounds into formulations for delivery to the site of action. Suitable formulations for parenteral administration include aqueous solutions of the active compounds in water-soluble form; for example, water-soluble salts. Oily injection suspensions of the active compounds may also be administered. Suitable lipophilic solvents or vehicles include fatty oils, such as sesame oil or synthetic fatty acid esters (e.g., ethyl oleate or triglycerides). Aqueous injection suspensions can contain substances that increase the viscosity of the suspension. These include, for example, sodium carboxymethyl cellulose, sorbitol, and dextran. Optionally, the suspension can also contain stabilizers. The compositions can also include solubilizing agents (e.g., cyclodextrins) for improving the amount of the antagonist(s) dissolved (i.e., rather than suspended) in a liquid component of the composition.

The pharmaceutical formulation for systemic administration as disclosed herein can be formulated for enteral, parenteral, or topical administration. Indeed, all three types of formulations can be used simultaneously to achieve systemic administration of the active ingredient.

Suitable formulations for oral administration include hard or soft gelatin capsules, pills, tablets, including coated tablets, elixirs, suspensions, syrups or inhalations and controlled release forms thereof.

The compounds described herein can also be incorporated into pharmaceutical compositions which allow for sustained delivery of those compounds to a mammal for a period of several days, several weeks, or a month or more. Such formulations are described, for example, in U.S. Pat. Nos. 5,968,895 and 6,180,608 and are otherwise known in the art. Any pharmaceutically-acceptable, sustained-release formulation known in the art is contemplated.

For topical administration, any common topical formulation such as a solution, suspension, gel, ointment, salve, or similar composition can be employed. Preparations of such topical formulations are described in the art of pharmaceutical formulations as exemplified, for example, by Remington, 2006, *The Science and Practice of Pharmacy,* 21st Edition, Lippincott Williams & Wilkins. For topical application, the antagonists as disclosed herein can be administered as a powder or spray, particularly in aerosol form, for example.

The active ingredient can also be administered in pharmaceutical compositions adapted for systemic administration. If a drug is to be administered systemically, it can be confected as a powder, pill, tablet, or other solid composition or as a syrup, elixir, or other liquid composition for oral administration. For intravenous, intraperitoneal, or intra-lesional administration, the active ingredient is prepared as a solution or suspension capable of being administered by injection. In certain cases, it can be useful to formulate the active ingredient in suppository form or as an extended release formulation for deposit under the skin or intramuscular injection.

The compounds described herein can be administered by inhalation. For inhalation therapy, the compound can be in a solution useful for administration by metered dose inhalers or in a form suitable for a dry powder inhaler, for example.

Pharmaceutical compositions expressly include both those formulated and intended for administration to humans and veterinary compositions formulated and intended for administration to non-human animals.

The compounds disclosed herein (as well as their pharmaceutically acceptable salts and compositions including the same) can be administered to a wide variety of subjects.

Expressly contemplated approaches for administering the compounds and compositions described herein include delivery by either the parenteral or oral route, intramuscular injection, subcutaneous/intradermal injection, intravenous injection, buccal administration, transdermal delivery and administration by the rectal, colonic, vaginal, intranasal or respiratory tract route (e.g., by inhalation).

It is contemplated that the compounds disclosed herein are administered in a therapeutically effective amount. The effective amount of the compounds and compositions described herein or pharmaceutically acceptable salts thereof as described herein may be determined by one of ordinary skill in the art and includes exemplary dosage amounts for a mammal of from about 0.5 to about 200 mg/kg of body weight of active compound per day, which may be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day.

Those of skill in the art will understand that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

IV. METHODS OF MAKING THE COMPOUNDS

The compounds described herein can be prepared in a variety of ways known to one skilled in the art of organic synthesis or variations thereon as appreciated by those skilled in the art. The compounds described herein can be prepared from readily available starting materials. Optimum reaction conditions may vary with the particular reactants or solvents used, but such conditions can be determined by one skilled in the art.

Variations on Formula I, Formula II, Formula III, Formula IV, Formula V, Formula VI, Formula VII, and Formula VIII include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^{1}H$ or $^{13}C$) infrared spectroscopy, spectrophotometry (e.g., UV-visible), or mass spectrometry, or by chromatography such as high performance liquid chromatograpy (HPLC) or thin layer chromatography.

The compounds described by Formula I can be made, for example, by treating a mixture of 2-naphthol and formaldehyde aqueous solution with an amine. In some examples, the molar ratio of 2-naphthol to the amine can be 2:1. Further examples of Formula I can be prepared, for example, through the acetylation or methylation of hydroxyl groups on the compounds. Detailed experimental procedures for synthesizing the compounds described herein can be found in Example 3.

V. METHODS OF USE

Provided herein are methods to treat, prevent, or ameliorate giardiasis in a subject. The methods include administering to a subject an effective amount of one or more of the compounds or compositions described herein, or a pharmaceutically acceptable salt or prodrug thereof. The compounds and compositions described herein or pharmaceutically acceptable salts thereof are useful for treating giardiasis in humans, e.g., pediatric and geriatric populations, and in animals, e.g., veterinary applications. Also provided herein are methods of inhibiting or antagonizing *Giardia lamblia* attachment to the intestinal wall of a subject. The methods comprise administering to a subject an effective amount of one or more of the compounds or compositions described herein, or a pharmaceutically acceptable salt or prodrug thereof.

The effectiveness of the compounds and compositions described herein in treating, preventing, or ameliorating giardiasis and for antagonizing *Giardia lamblia* attachment to the intestinal wall of a subject can be measured according to one of several standard measures as known to persons of skill in the art. For example, parasite burden can be measured directly in animal models of infection by counting parasites at the trophozoite stage within the lumen of the small intestine. A method of measuring parasite burden indirectly in both animal and human infections can be performed by determining cyst output in feces, which is also a measure of transmission. In addition, the physiological effects of reduced parasite burden can be measured in animals through weight gain or diarrhea. Further, the physiological effects of reduced parasite burden can be measured in humans through alleviation of reported symptoms, reduction in duration and intensity of diarrhea, and weight gain. Such amounts are sufficient to achieve a therapeutically effective concentration of the compound or active component of the composition in vivo or in vitro.

These methods can further include treatment with one or more additional agents (e.g., an antibiotic, an antiparasitic, or an antiprotozoal). The one or more additional agents and the compounds and compositions or pharmaceutically acceptable salts thereof as described herein can be administered in any order, including simultaneous administration, as well as temporally spaced order of up to several days apart. The methods may also include more than a single administration of the one or more additional agents and/or the compounds and compositions or pharmaceutically acceptable salts thereof as described herein. The administration of the one or more additional agents and the compounds and compositions or pharmaceutically acceptable salts thereof as described herein may be by the same or different routes. When treating with one or more additional agents, the compounds and compositions or pharmaceutically acceptable salts thereof as described herein can be combined into a pharmaceutical composition that includes the one or more additional agents. For example, the compounds and compositions or pharmaceutically acceptable salts thereof as described herein can be combined into a pharmaceutical composition with an antibiotic, for example, metronidazole, furazolidone, or paramomycin. In other examples, the compounds and compositions or pharmaceutically acceptable salts thereof as described herein can be combined into a pharmaceutical composition with an antiparasitic, for example, tinidazole or mebendazole. Further, the compounds and compositions or pharmaceutically acceptable salts thereof as described herein can be combined into a pharmaceutical composition with an antiprotozoal agent, for example, nitazoxanide or quinacrine.

The methods and compounds as described herein are useful for both prophylactic and therapeutic treatment. For prophylactic use, a therapeutically effective amount of the compounds and compositions or pharmaceutically acceptable salts thereof as described herein are administered to a subject prior to onset (e.g., before obvious signs of giardiasis), during early onset (e.g., upon initial signs and symptoms of giardiasis), or after an established microbial infection or development of giardiasis. Prophylactic administration can occur for several days to years prior to the manifestation of symptoms of an infection. Prophylactic administration can be used, for example, in the preventative treatment of subjects exposed to *Giardia lamblia*. Therapeutic treatment involves administering to a subject a therapeutically effective amount of the compounds and compositions or pharmaceutically acceptable salts thereof as described herein after giardiasis is diagnosed.

VI. KITS

Also provided herein are kits for treating or preventing giardiasis in a subject. A kit can include any of the compounds or compositions described herein. For example, a kit can include a compound of Formula I, Formula II, Formula III, Formula IV, Formula V, Formula VI, Formula VII, Formula VIII, or combinations thereof. A kit can further include one or more additional agents, such as an antibiotic agent (e.g., metronidazole, furazolidone, or paromomycin), an antiparasitic agent (e.g., tinidazole or mebendazole), and/or an antiprotozoal agent (e.g., nitazoxanide or quinacrine). A kit can include an oral formulation of any of the compounds or compositions described herein. A kit can additionally include directions for use of the kit (e.g., instructions for treating a subject), a container, a means for administering the compounds or compositions, and/or a carrier.

EXAMPLES

Example 1

Lead Compound Identification

The NCI Diversity Set:

The NCI Diversity Set (now known as NCI Diversity Set I) is comprised of ~1990 molecules pre-plated in groups of 80 in 96-well plates at 10 mM. An initial catalog of –140,000 "open repository" compounds was narrowed to ~72,000 based on compound availability. Chem-X was used to select the ~1990 compounds representing the greatest pharmocophore diversity.

*Giardia* Attachment:

A phenotype-based screen, using polystyrene microplates, of the ~1990 compounds in the NCI Diversity Set was developed to identify compounds that block the ability of the parasites to attach to an inert substrate. About 100,000 late-log stage parasites were added to each well and allowed to attach at 37° C. for 2 hours. Plates were washed twice with warm PBS to remove detached cells, fixed in 1:1 methanol: acetone for 3-5 minutes, and incubated with 8 μM Syto 16 nucleic acid stain for 30 minutes. Automated fluorescent images (4/well for ~20% well surface area) were captured at 10× using a GFP filter with the Nikon Eclipse TE-300 inverted microscope and analyzed using METAMORPH "count nuclei" software (Molecular Devices, Inc.; Sunnyvale, Calif.). The compounds were tested in triplicate at 50 μM. The effect of each compound on attachment was quantified using median values of the percentage of parasites attached in treated-wells relative to the untreated-well in that row in the 96-well plate; DMSO alone exhibited no significant effect on attachment. A total of 85 compounds reduced attachment by ≥80%, and an additional 142 compounds reduced attachment between 50-80%. These 227 compounds (~11%) were selected for further analysis.

IEC-6 Viability and Attachment:

Adherent monolayers of IEC-6 cells, a rat small intestinal cell line, were treated with 50 μM of the 227 compounds identified as "primary hits" in the *Giardia* attachment screen as done for the *Giardia* cultures. Cells were then stained for 20 min at 37° C. with a 1:500 dilution of DEAD Red, a membrane-impermeant nucleic acid stain, fixed in 4% gluteraldehyde, and labeled for 20 min at 20° C. with 8 μM SYTO 16, a membrane-permeant nucleic acid stain. This dual stain approach demonstrated the IEC-6 cell death that results either in detachment or changes to membrane permeability. Of the 227 compounds analyzed, 134 had a significant negative effect on the IEC-6 cells (attachment<50% and viability<75%) and were therefore eliminated from further study. Ninety-three compounds had only a weak or moderate effect on IEC-6 cells (attachment≥50% and viability≥75%) and were retained for further study.

Dose-Dependent Determination of Efficacy of Compounds to Define Top Candidates:

A single concentration of 50 μM of the compounds that would be particularly stringent in assaying for IEC-6 viability was used for the remainder of the screening process. To define compounds most effective at the lowest concentrations, $IC_{50}$ assays were conducted as described above against the 93 compounds that passed the IEC-6 screen. Parametric and non-parametric statistical analyses were performed as appropriate to determine the statistical significance of the data, and statistical significance was reported when $P<0.05$. By choosing only those compounds that had a statistically significant reduction of parasite attachment at 5 μM, the list of lead candidates was narrowed to seven compounds. Each compound retained ≥85% IEC-6 attachment and viability.

Example 2

Effect of Compounds I-16, III-1, IV-1, V-1, VI-1, VII-1, and VIII-2A on *Giardia lamblia* Attachment

*Giardia* Attachment:

Approximately 100,000 late-log stage *Giardia lamblia* parasites were added to individual wells of polystyrene microplates and allowed to attach to the microplates at 37° C. for 2 hours. The microplates were washed twice with warm PBS to remove detached cells, fixed in 1:1 methanol:acetone for 3-5 minutes, and incubated with 8 μM Syto 16 nucleic acid stain for 30 minutes. Automated fluorescent images (4/well for ~20% well surface area) were captured at 10× using a GFP filter with the Nikon ECLIPSE TE-300 inverted microscope (Nikon Inc.; Melville, N.Y.) and analyzed using Metamorph™ "count nuclei" software.

Compounds I-16, III-1, IV-1, V-1, VI-1, VII-1, and VIII-2A were applied to wells in triplicate at a concentration of 50 μM. The effect of each compound on the attachment of *Giardia lamblia* parasites was evaluated using median values of the percentage of parasites attached in treated-wells relative to an adjacent untreated-well. DMSO was used as a control, and exhibited no significant effect on attachment. Each of Compounds I-16, III-1, IV-1, V-1, VI-1, VII-1, and VIII-2A reduced the attachment of *Giardia lamblia* parasites by at least 80%.

Short-Term Effect of Compounds I-16, IV-1, V-1, VI-1, VII-1, and VIII-2A on IE-6 viability and attachment:

Adherent monolayers of IEC-6 cells, a rat small intestinal cell line, were treated for two hours with 50 μM of Compounds I-16, III-1, IV-1, V-1, VI-1, VII-1, and VIII-2A in phosphate buffered saline (PBS). Cells were then stained for 20 min at 37° C. with a 1:500 dilution of DEAD Red, a membrane-impermeant nucleic acid stain, fixed in 4% gluteraldehyde, and labeled for 20 min at 20° C. with 8 μM SYTO 16, a membrane-permeant nucleic acid stain. This dual stain approach permitted the visualization of IEC-6 cell death leading to either detachment or changes to membrane permeability. Each of Compounds I-16, III-1, IV-1, V-1, VI-1, VII-1, and VIII-2A had a only a weak or moderate effect on IEC-6 cells, as in every case at least 50% of cells remained attached and at least 75% of cells remained viable after exposure to each compound.

Long-term Effect of Compounds I-16, IV-1, V-1, VI-1, VII-1, and VIII-2A on IEC-6 viability and attachment:

Adherent monolayers of IEC-6 cells, a rat small intestinal cell line, were treated for 2-48 hours with 50 μM of Compounds I-16, III-1, IV-1, V-1, VI-1, VII-1, and VIII-2A in culture media. Viability was measured by the ability of living cells to exclude 0.4% Trypan Blue dye. All comparisons were made to cultures of untreated IEC-6 cells. Each of Compounds I-16, III-1, IV-1, V-1, VI-1, VII-1, and VIII-2A had only a weak effect on IEC-6 cells, as in every case at least 75% of cells remained attached and at least 75% of cells remained viable after exposure to each compound.

Dose-Dependent Efficacy of Compounds I-16, III-1, IV-1, V-1, VI-1, VII-1, and VIII-2A:

As shown in FIG. 1, the dose-dependency of each of Compounds I-16, III-1, IV-1, V-1, VI-1, VII-1, and VIII-2A was evaluated by examining the effect of each compound at 50, 15, 10, 5 and 1 μM. Mercury was used as a control. In the case of each compound, amounts as low as 5 μM reduced *Giardia* attachment by at least 50%, while at least 85% of IEC-6 cells remained attached and viable. This indicates that each of Compounds I-16, III-1, IV-1, V-1, VI-1, VII-1, and VIII-2A are effective in antagonizing *Giardia* attachment to the intestinal wall without impacting the viability of the intestinal wall. Accordingly, Compounds I-16, III-1, IV-1, V-1, VI-1, VII-1, and VIII-2A are suitable for use in therapeutic compositions and methods such as those described herein.

Examination of Parasite Morphology and Dynamics in the Presence of Compounds I-16, III-1, IV-1, V-1, VI-1, VII-1, and VIII-2A:

A series of video microscopy studies were undertaken to examine the effect of the compounds on parasite morphology and dynamics. Short 1 minute videos of parasite behavior were recorded using DIC optics on a Zeiss AXIOPLAN microscope (Carl Zeiss Microimaging GmbH, Germany) using a Photometrics CCD camera (Photometrics, Inc.; Tucson, Ariz.). Recordings were made on at least three separate occasions at compound concentrations of 50 μM, 15 μM, 10 μM, 5 μM, and 1 μM to allow comparison to the dose-response curves in the attachment assay. Four broad categories of compound action were found (see Table I).

TABLE I

| Observed Parasite Morphology and Dynamics | Compound ID |
|---|---|
| Parasites display a profoundly disrupted morphology and/or are simply destroyed. | III-1, IV-1 |
| Parasites display disrupted peripheral morphology, resulting in loss of shape or localized membrane blebbing. | VI-1, VII-1 |
| Parasites appear normal in morphology, but are paralyzed (i.e. no flagellar beating). | V-1 |
| Parasites appear normal in morphology and activity, but exhibit reduced attachment. | I-16, VIII-2A |

Each of Compounds I-16, III-1, IV-1, V-1, VI-1, VII-1, and VIII-2A affected *Giardia* attachment at concentrations of 5 μM without impacting viability of an intestinal epithelial cell line in one of four ways. Compounds III-1 and IV-1 profoundly disrupted parasite morphology or simply destroyed the parasites. Compounds V-1 and VI-1 caused the parasites to display a disrupted peripheral morphology, resulting either in loss of overall shape or localized membrane blebbing. Compound VII-1 caused no observable effect on *Giardia* morphology, but did cause flagellar paralysis, and Compounds I-16 and VIII-2A produced no observable effect on parasite morphology and activity, but did significantly reduce attachment. Reversibility of Compounds I-16, III-1, IV-1, V-1, VI-1, VII-1, and VIII-2A on *Giardia* viability and attachment:

Parasite cultures were treated for 30 minutes—2 hours with 15 μM of Compounds I-16, III-1, IV-1, V-1, VI-1, VII-1, and VIII-2A in PBS at 37° C. Parasites were then washed with warm PBS to remove compounds, and were placed in normal *Giardia* growth media for an additional 48 hours. Parasite cultures were observed at regular intervals to determine attachment, and viability was measured by the ability of the parasites to exclude 0.4% Trypan Blue dye. All comparisons were made to cultures of untreated *Giardia*. Compounds I-16, III-1, IV-1, V-1, VI-1, VII-1, and VIII-2A differed in their reversibility: Compounds III-1 and IV-1 appeared to be irreversible in their effect on parasite attachment and viability, while Compounds I-16, V-1, VI-1, VIM, and VIII-2A were largely reversible.

Example 3

Synthesis and NMR Characterization

All commercially available reagents and solvents were used without further purification. NMR spectra were obtained at 400 MHz ($^1$H NMR). Chemical shifts are reported in ppm relative to TMS. Reaction products were purified by column chromatography on silica gel (particle size 32-63 μm) or recrystallization.

Compound I-1:

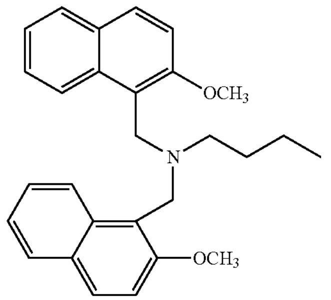 [SMILES: CCCCN(Cc1c(OC)ccc2ccccc12)Cc1c(OC)ccc2ccccc12]

To a solution of Compound I-18 (140 mg, 0.36 mmol) in 2 mL of DMF were added 54.6 mg of potassium carbonate (1.1 equivalents) and 102 mg of methyl iodide (2 equivalents). The reaction mixture was stirred for 8 h at room temperature and extracted with ethyl acetate and water. Column chromatography with EtOAc:hexanes=1:4 as mobile phase provided 54 mg (0.13 mmol) of a yellow solid in 36% yield. $^1$H NMR (400 MHz, $CDCl_3$) δ=0.71 (t, J=7.4 Hz, 3H), 1.10 (m, 2H), 1.62 (m, 2H), 2.52 (t, J=7.3 Hz, 2H), 3.91 (s, 6H), 4.05 (s, 4H), 7.01 (dd, J=7.5 Hz, 7.8 Hz, 2H), 7.20-7.23 (m, 4H), 7.69 (d, J=8.2 Hz, 2H), 7.73 (d, J=8.0 Hz, 2H), 7.78 (d, J=8.6 Hz, 2H).

Compound I-2:

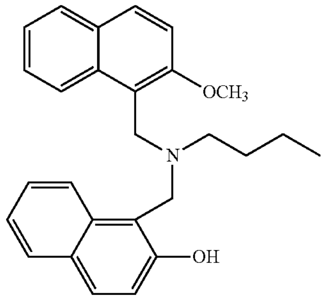 [SMILES: CCCCN(Cc1c(O)ccc2ccccc12)Cc1c(OC)ccc2ccccc12]

To a solution of Compound I-18 (114 mg, 0.30 mmol) in 2 mL of DMF were added 45 mg of potassium carbonate (1.1 equivalents) and 46 mg of methyl iodide (1.1 equivalents). The reaction mixture was stirred overnight at room temperature and extracted with ethyl acetate and water. Column chromatography with EtOAc:hexanes=1:9 as mobile phase provided 39 mg (0.1 mmol) of a white solid in 33% yield. $^1$H NMR (400 MHz, $CDCl_3$) δ=0.84 (t, J=7.3 Hz, 3H), 1.24 (m, 2H), 1.74 (m, 2H), 2.65 (t, J=7.31 Hz, 2H), 3.99 (s, 3H), 4.17 (s, 2H), 4.25 (s, 2H), 6.96 (d, J=8.9 Hz, 1H), 7.20-7.28 (m, 2H), 7.33-7.42 (m, 2H), 7.54-7.58 (m, 2H), 7.68 (d, J=7.9 Hz, 1H), 7.77 (d, J=9.1 Hz, 1H), 7.80 (d, J=9.1 Hz, 1H), 7.85 (d, J=8.6 Hz, 1H), 8.12 (d, J=8.8 Hz, 1H).

Compound I-3:

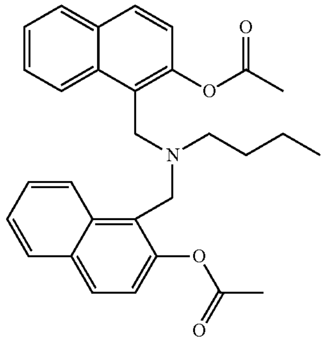 [SMILES: CCCCN(Cc1c(OC(C)=O)ccc2ccccc12)Cc1c(OC(C)=O)ccc2ccccc12]

To a solution of Compound I-18 (123 mg, 0.32 mmol) in 4 mL of anhydrous chloroform were added 76 mg of acetic acid (4 equivalents), 243 mg of EDC (4 equivalents), 20 mmol % of DMAP and 163 mg of DIEA (4 equivalents). The reaction mixture was stirred at room temperature for 72 hours and extracted with dichloromethane and water. Column chromatography with EtOAc:hexanes=1:5 as mobile phase provided 120 mg (0.26 mmol) of a white solid in 81% yield. $^1$H NMR (400 MHz, $CDCl_3$) δ=0.72 (t, J=7.3 Hz, 3H), 1.13 (m, 2H), 1.58 (m, 2H), 2.44 (t, J=8.3 Hz, 2H), 3.36 (s, 6H), 3.88 (s, 4H), 7.10 (ddd, J=1.1 Hz, 8.5 Hz, 8.5 Hz, 2H), 7.16 (d, J=8.9 Hz, 2H), 7.38 (ddd, J=1.1 Hz, 8.5 Hz, 8.5 Hz, 2H), 7.76 (d, J=8.9 Hz, 2H), 7.77 (d, J=8.0 Hz, 2H), 7.87 (d, J=8.6 Hz, 2H).

General Procedure for the Synthesis of Compounds I-4 to I-16, I-18, and I-21:

A solution of the 2-naphthol, formaldehyde aqueous solution (37%) and the amine (molar ratio=2:2:1) in methanol was stirred at room temperature. The reaction was followed by TLC and was generally complete between 2 and 24 hours. Upon completion, the product was isolated by filtration, washed with methanol, and purified by recrystallization as needed.

Compound I-4:

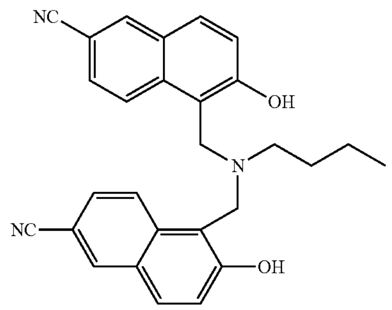 [SMILES: CCCCN(Cc1c(O)ccc2cc(C#N)ccc12)Cc1c(O)ccc2cc(C#N)ccc12]

The general procedure gave 210 mg (0.48 mmol) of a white solid in 28% yield. $^1$H NMR (400 MHz, DMSO-$d_6$) δ=0.67 (t, J=7.3 Hz, 3H), 1.09 (m, 2H), 1.56 (m, 2H), 2.53 (t, J=7.3 Hz, 2H), 4.10 (s, 4H), 7.18 (d, J=8.9 Hz, 2H), 7.52 (d, J=8.9 Hz, 2H), 7.81 (d, J=9.0 Hz, 2H), 7.95 (d, J=8.8 Hz, 2H), 8.35 (s, 2H).

Compound I-5:

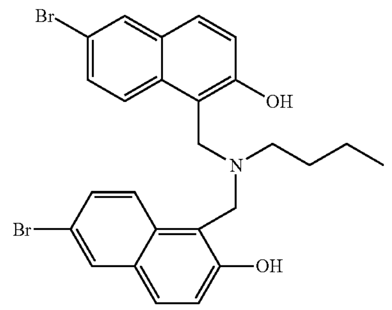 [SMILES: CCCCN(Cc1c(O)ccc2cc(Br)ccc12)Cc1c(O)ccc2cc(Br)ccc12]

The general procedure gave 574 mg (1.06 mmol) of a yellow solid in 62% yield. $^1$H NMR (400 MHz, DMSO-$d_6$) δ=0.68 (t, J=7.4 Hz, 3H), 1.10 (m, 2H), 1.56 (m, 2H), 2.51 (t, J=7.5 Hz, 2H), 4.05 (s, 4H), 7.09 (d, J=8.9 Hz, 2H), 7.37 (dd, J=2.1 Hz, 9.1 Hz, 2H), 7.66 (d, J=8.1 Hz, 2H), 7.78 (d, J=9.2 Hz, 2H), 8.00 (d, J=2.0 Hz, 2H), 10.8 (bs, 2H).

Compound I-6:

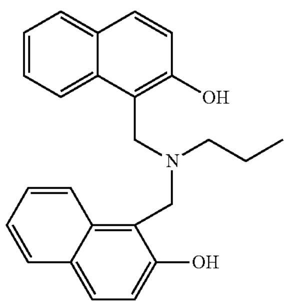 [SMILES: CCCN(Cc1c(O)ccc2ccccc12)Cc1c(O)ccc2ccccc12]

The general procedure gave 397 mg (1.07 mmol) of a white solid in 59% yield. $^1$H NMR (400 MHz, DMSO-$d_6$) δ=0.70 (t, J=7.2 Hz, 3H), 1.64 (m, 2H), 2.50 (t, J=7.6 Hz, 2H), 4.12 (s, 4H), 7.02 (d, J=8.9 Hz, 2H), 7.22 (dd, J=7.2 Hz, 7.5 Hz, 2H), 7.33 (dd, J=7.4 Hz, 7.5 Hz, 2H), 7.65 (d, J=8.9 Hz, 2H), 7.72 (d, J=8.0 Hz, 2H), 7.89 (d, J=8.5 Hz, 2H), 10.8 (bs, 2H).

Compound I-7:

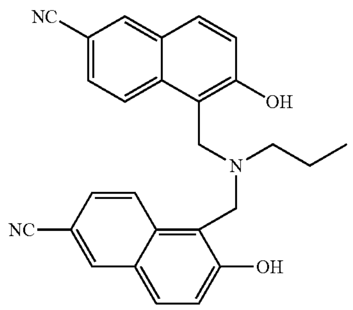 [SMILES: CCCN(Cc1c(O)ccc2cc(C#N)ccc12)Cc1c(O)ccc2cc(C#N)ccc12]

The general procedure gave 315 mg (1.34 mmol) of a yellow solid in 43% yield. $^1$H NMR (400 MHz, DMSO-$d_6$) δ=0.68 (t, J=7.2 Hz, 3H), 1.60 (m, 2H), 2.50 (t, J=10.3 Hz, 2H), 4.11 (s, 4H), 7.18 (d, J=8.9 Hz, 2H), 7.51 (dd, J=1.6 Hz, 8.8 Hz, 2H), 7.81 (d, J=9.0 Hz, 2H), 7.96 (d, J=8.8 Hz, 2H), 8.36 (d, J=1.5 Hz, 2H).

Compound I-8:

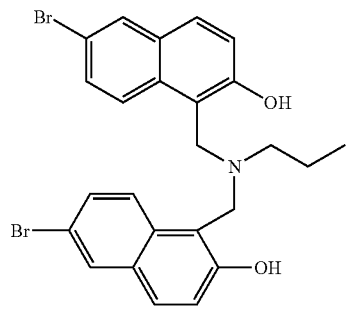 [SMILES: CCCN(Cc1c(O)ccc2cc(Br)ccc12)Cc1c(O)ccc2cc(Br)ccc12]

The general procedure gave 429 mg (0.81 mmol) of a light yellow solid in 47% yield. $^1$H NMR (400 MHz, DMSO-$d_6$) δ=0.68 (t, J=7.2 Hz, 3H), 1.60 (m, 2H), 2.47 (m, 2H), 4.07 (s, 4H), 7.09 (d, J=8.9 Hz, 2H), 7.38 (dd, J=2.1 Hz, 9.1 Hz, 2H), 7.66 (d, J=8.9 Hz, 2H), 7.78 (d, J=9.7 Hz, 2H), 7.99 (d, J=2.0 Hz, 2H), 10.80 (bs, 2H).

Compound I-9:

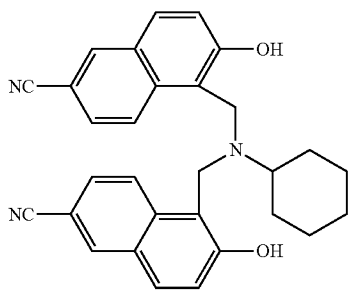 [SMILES: N#Cc1ccc2c(CN(Cc3c(O)ccc4cc(C#N)ccc34)C3CCCCC3)c(O)ccc2c1]

The general procedure gave 370 mg (0.80 mmol) of a white solid in 49% yield. $^1$H NMR (400 MHz, DMSO-$d_6$) δ=0.95-1.15 (m, 3H), 1.44-1.66 (m, 3H), 1.74 (d, J=10.9 Hz, 2H), 2.02 (d, J=10.9 Hz, 2H), 2.53 (t, J=11.8 Hz, 1H), 4.16 (s, 4H), 7.09 (d, J=8.9 Hz, 2H), 7.50 (d, J=8.8 Hz, 2H), 7.75 (d, J=9.0 Hz, 2H), 7.96 (d, J=8.9 Hz, 2H), 8.29 (s, 2H), 11.55 (bs, 2H).

Compound I-10:

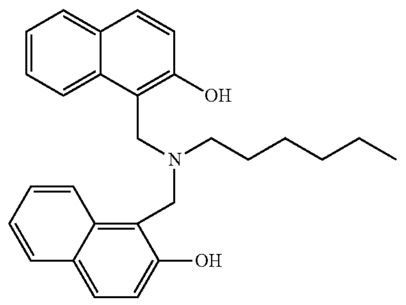 [SMILES: CCCCCCN(Cc1c(O)ccc2ccccc12)Cc1c(O)ccc2ccccc12]

The general procedure gave 52 mg (0.13 mmol) of a white solid in 47% yield. $^1$H NMR (400 MHz, DMSO-$d_6$) δ=0.71 (t, J=7.2 Hz, 3H), 1.00-1.12 (m, 6H), 1.60 (m, 2H), 2.54 (t, J=6.8 Hz, 2H), 4.12 (s, 4H), 7.04 (d, J=8.8 Hz, 2H), 7.21-7.26 (m, 2H), 7.31-7.36 (m, 2H), 7.66 (d, J=8.8 Hz, 2H), 7.73 (d, J=7.4 Hz, 2H), 7.90 (d, J=8.5 Hz, 2H), 10.75 (bs, 2H).

Compound I-11:

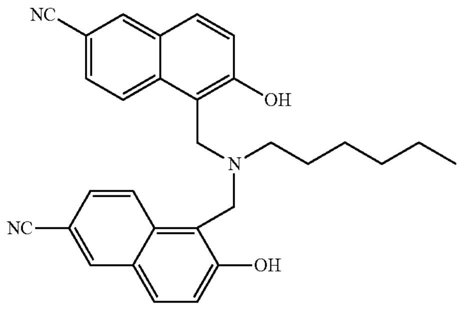 [SMILES: CCCCCCN(Cc1c(O)ccc2cc(C#N)ccc12)Cc1c(O)ccc2cc(C#N)ccc12]

The general procedure gave 117 mg (0.25 mmol) of a yellow solid in 44% yield. $^1$H NMR (400 MHz, DMSO-$d_6$) δ=0.68 (t, J=7.1 Hz, 3H), 0.92-1.08 (m, 6H), 1.54 (m, 2H), 2.50 (t, 0.1=7.4 Hz, 2H), 4.09 (s, 4H), 7.19 (d, J=8.9 Hz, 2H), 7.49 (d, J=8.8 Hz, 2H), 7.81 (d, J=8.8 Hz, 2H), 7.95 (d, J=8.8 Hz, 2H), 8.35 (s, 2H), 11.25 (bs, 2H).

Compound I-12:

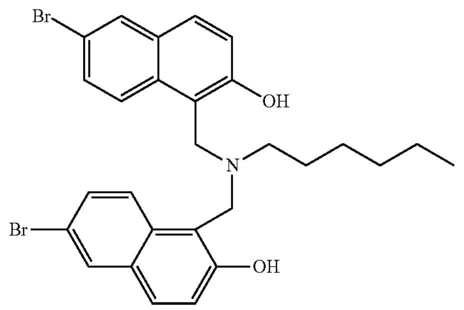 [SMILES: CCCCCCN(Cc1c(O)ccc2cc(Br)ccc12)Cc1c(O)ccc2cc(Br)ccc12]

The general procedure gave 396 mg (0.69 mmol) of a white solid in 39% yield. $^1$H NMR (400 MHz, DMSO-$d_6$) δ=0.69 (t, J=7.2 Hz, 3H), 0.95-1.10 (m, 6H), 1.54 (m, 2H), 2.49 (t, J=9.2 Hz, 2H), 4.06 (s, 4H), 7.08 (d, J=8.8 Hz, 2H), 7.35 (dd, J=2.1 Hz, 9.1 Hz, 2H), 7.65 (d, J=8.9 Hz, 2H), 7.78 (d, J=9.2 Hz, 2H), 8.00 (d, J=2.1 Hz, 2H), 11.76 (bs, 2H).

Compound I-13:

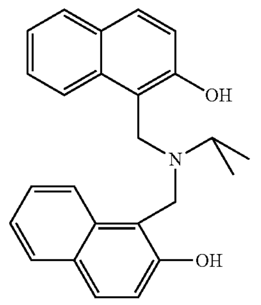 [SMILES: CC(C)N(Cc1c(O)ccc2ccccc12)Cc1c(O)ccc2ccccc12]

The general procedure gave 287 mg (0.77 mmol) of a white solid in 45% yield. $^1$H NMR (400 MHz, DMSO-$d_6$) δ=1.24 (d, J=6.6 Hz, 6H), 2.96 (m, 1H), 4.11 (s, 4H), 6.99 (d, J=8.1 Hz, 2H), 7.22 (dd, J=7.2 Hz, 7.6 Hz, 2H), 7.36 (dd, J=7.2 Hz, 8.0 Hz, 2H), 7.63 (d, J=8.8 Hz, 2H), 7.71 (d, J=7.9 Hz, 2H), 7.94 (d, J=8.5 Hz, 2H), 10.96 (bs, 2H).

Compound I-14:

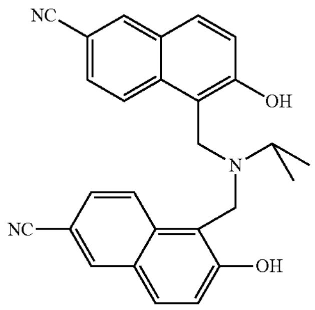 [SMILES: CC(C)N(Cc1c(O)ccc2cc(C#N)ccc12)Cc1c(O)ccc2cc(C#N)ccc12]

The general procedure gave 23 mg (0.05 mmol) of a yellow solid in 28% yield. $^1$H NMR (400 MHz, DMSO-$d_6$) δ=1.24 (d, J=6.1 Hz, 6H), 2.96 (m, 1H), 4.12 (s, 4H), 7.12 (d, J=6.8 Hz, 2H), 7.53 (d, J=8.8 Hz, 2H), 7.77 (d, J=8.9 Hz, 2H), 8.02 (d, J=7.1 Hz, 2H), 8.31 (s, 2H), 11.60 (bs, 2H).

Compound I-15:

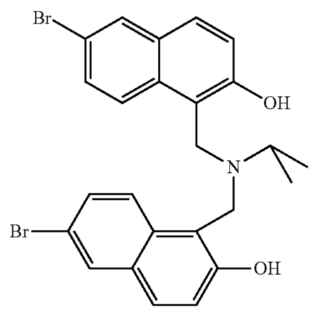 [SMILES: CC(C)N(Cc1c(O)ccc2cc(Br)ccc12)Cc1c(O)ccc2cc(Br)ccc12]

The general procedure gave 24 mg (0.05 mmol) of a yellow solid in 33% yield. $^1$H NMR (400 MHz, DMSO-$d_6$) δ=1.22 (d, J=6.6 Hz, 6H), 2.94 (m, 1H), 4.07 (s, 4H), 7.04 (d, J=8.9 Hz, 2H), 7.40 (dd, J=1.8 Hz, 9.1 Hz, 2H), 7.64 (d, J=9.0 Hz, 2H), 7.84 (d, J=9.1 Hz, 2H), 7.98 (d, J=1.8 Hz, 2H), 11.02 (bs, 2H).

Compound I-16:

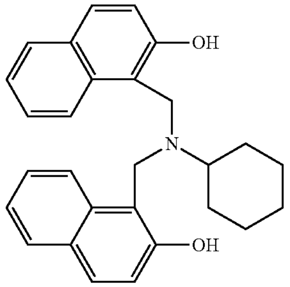 [SMILES: Oc1ccc2ccccc2c1CN(Cc1c(O)ccc2ccccc12)C1CCCCC1]

The general procedure gave 23 mg (0.06 mmol) of a yellow solid in 33% yield. $^1$H NMR (400 MHz, DMSO-$d_6$) δ=0.95-1.12 (m, 3H), 1.52 (d, J=11.3 Hz, 1H), 1.65 (m, 2H), 1.77 (d, J=12.2 Hz, 2H), 2.14 (d, J=11.3 Hz, 1H), 2.57 (t, J=11.8 Hz, 1H), 4.18 (s, 4H), 6.99 (d, J=8.9 Hz, 2H), 7.23 (dd, J=6.7 Hz, 7.1 Hz, 2H), 7.35 (dd, J=7.2 Hz, 8.1 Hz, 2H), 7.65 (d, J=8.6 Hz, 2H), 7.73 (d, J=8.2 Hz, 2H), 7.91 (d, J=8.5 Hz, 2H), 11.96 (bs, 2H).

Compound I-18:

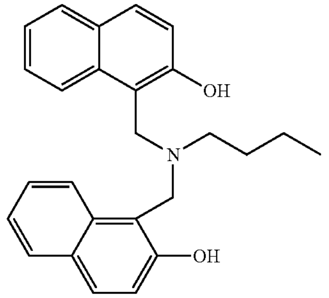 [SMILES: CCCCN(Cc1c(O)ccc2ccccc12)Cc1c(O)ccc2ccccc12]

The general procedure gave 311 mg (0.81 mmol) of a white solid in 81% yield. $^1$H NMR (400 MHz, $CDCl_3$) δ=0.85 (t, J=7.4 Hz, 3H), 1.28 (m, 2H), 1.79 (m, 2H), 2.75 (t, J=7.7 Hz, 2H), 4.12 (s, 4H), 7.02 (d, J=8.9 Hz, 2H), 7.30 (dd, J=7.3 Hz, 7.3 Hz, 2H), 7.50 (dd, J=7.5 Hz, 7.5 Hz, 2H), 7.59 (d, J=7.8 Hz, 2H), 7.73 (d, J=8.1 Hz, 2H), 7.98 (d, J=8.5 Hz, 2H).

Compound I-21:

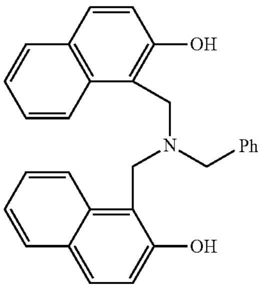 [SMILES: Oc1ccc2ccccc2c1CN(Cc1ccccc1)Cc1c(O)ccc2ccccc12]

The general procedure gave 95 mg (0.23 mmol) of a yellow solid in 45% yield. $^1$H NMR (400 MHz, DMSO-$d_6$) δ=3.63 (s, 2H), 4.01 (s, 4H), 7.05 (d, J=8.8 Hz, 2H), 7.13-7.21 (m, 4H), 7.26-7.36 (m, 5H), 7.56 (d, J=8.2 Hz, 2H), 7.65 (d, J=8.8 Hz, 2H), 730 (d, J=7.6 Hz, 2H), 10.4 (bs, 2H).

Compound I-22:

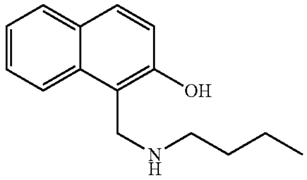 [SMILES: CCCCNCc1c(O)ccc2ccccc12]

To a solution of 2-naphthol (144 mg, 1 mmol) in 0.7 mL of methanol were added 81 mg of aqueous formaldehyde (37%) and 146 mg (2 mmol) of butyl amine and stirred at room temperature overnight. Column chromatography with EtOAc:hexanes=3:2 as mobile phase provided 18.3 mg (0.08 mmol) of a yellow oil in 8% yield. $^1$H NMR (400 MHz, $CDCl_3$) δ=0.93 (t, J=7.3 Hz, 3H), 1.39 (m, 2H), 1.58 (m, 2H), 2.76 (t, J=7.1 Hz, 3H), 4.45 (s, 2H), 7.09 (d, J=7.8 Hz, 1H), 7.27 (ddd, J=0.9 Hz, 7.9 Hz, 7.9 Hz, 1H), 7.42 (ddd, J=1.3 Hz, 6.8 Hz, 6.9 Hz, 1H), 7.66 (d, J=8.8 Hz, 1H), 7.74 (d, J=8.0 Hz, 1H), 7.78 (d, J=8.0 Hz, 1H).

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods and combinations of various features of the compounds and methods are intended to fall within the scope of the appended claims, even if not specifically recited. Thus, a combination of steps, elements, components, or constituents may be explicitly mentioned herein; however, all other combinations of steps, elements, components, and constituents are included, even though not explicitly stated.

What is claimed is:

1. A compound selected from the group consisting of:

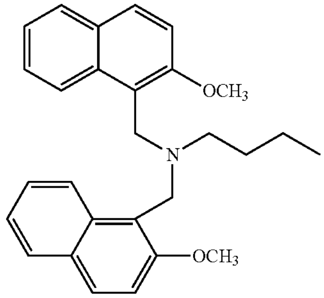

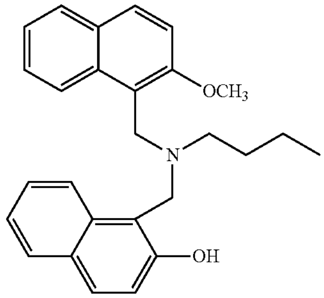

-continued

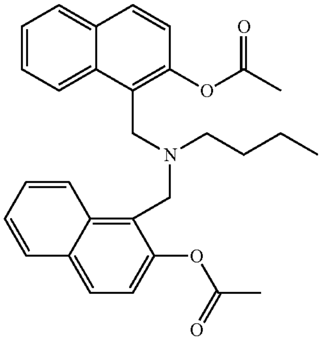

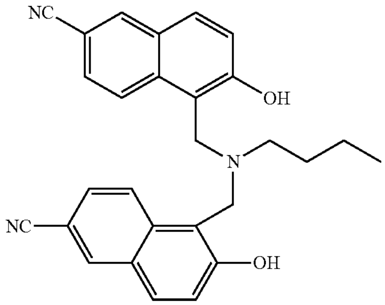

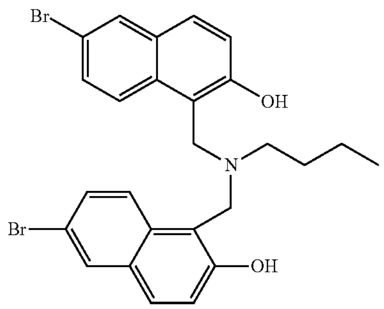

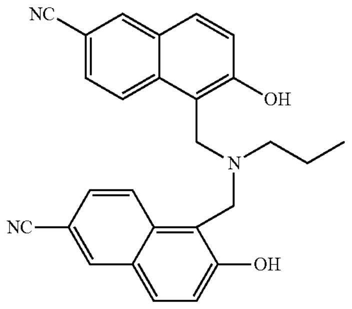

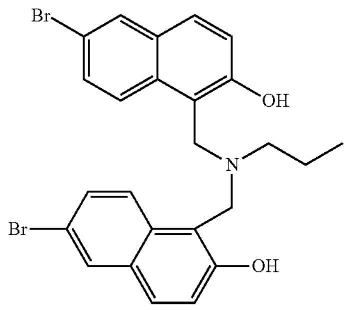

-continued

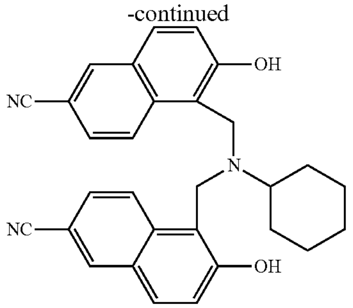

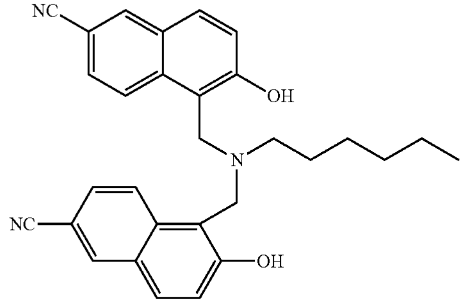

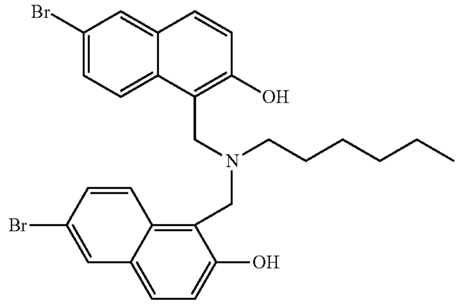

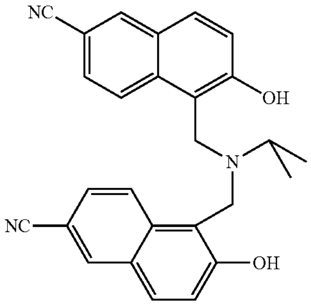

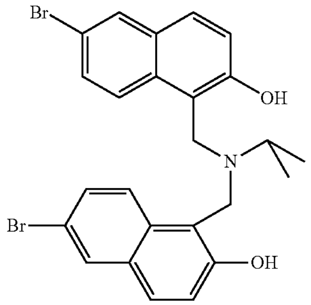

or a pharmaceutically acceptable salt or prodrug thereof.

2. A composition comprising a compound of claim 1 and a pharmaceutically acceptable carrier.

3. A method of treating giardiasis in a subject or antagonizing *Giardia lamblia* attachment to the intestinal wall of a subject, comprising:

administering to the subject a compound selected from the group consisting of:

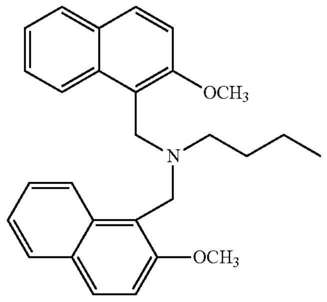
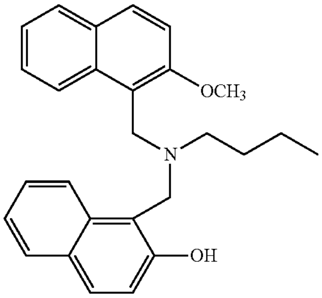
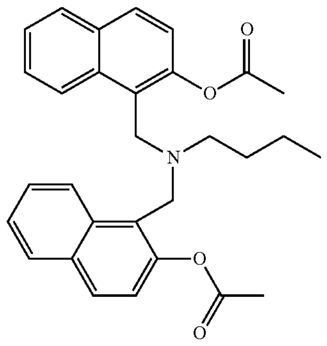
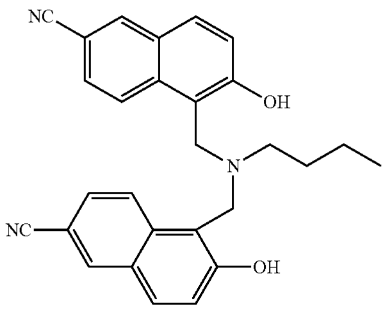
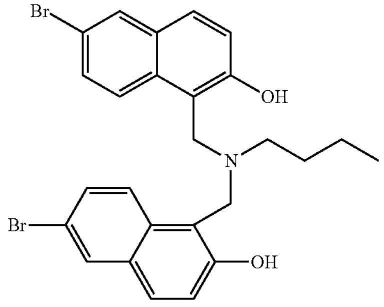
-continued
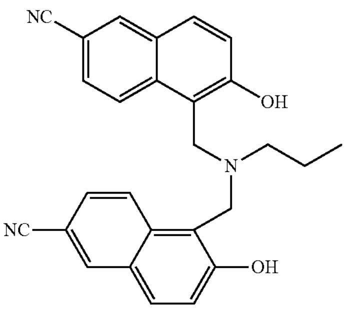
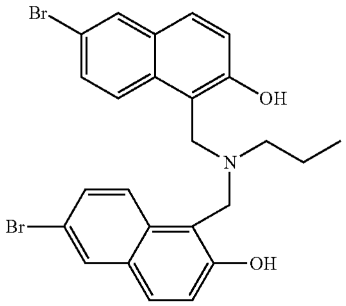
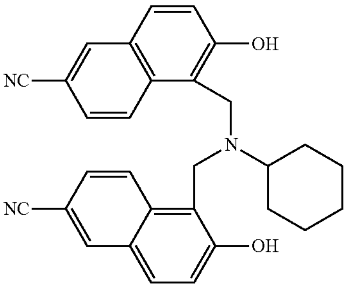
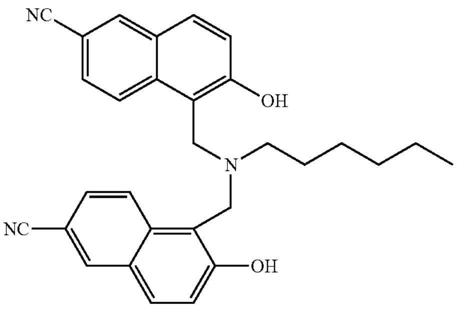
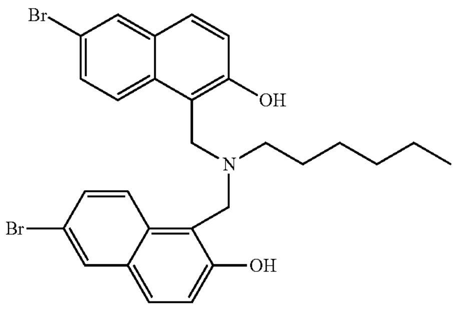

-continued
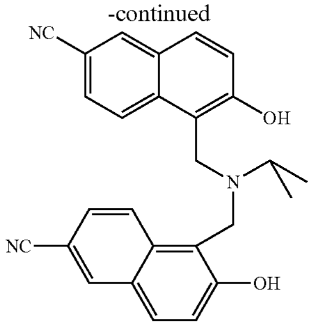
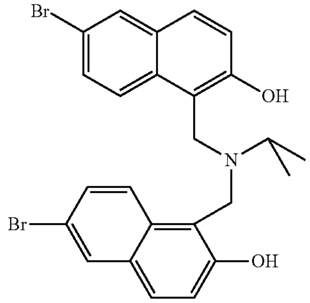
or a composition comprising the compound and a pharmaceutically acceptable carrier.
* * * * *